United States Patent
Kleinman

(10) Patent No.: US 8,398,717 B2
(45) Date of Patent: Mar. 19, 2013

(54) PARTIAL OR COMPLETE PROSTHETIC REPLACEMENT ARTHROPLASTY OF THE DISTAL RADIOULNAR JOINT

(75) Inventor: William B. Kleinman, Indianapolis, IN (US)

(73) Assignee: Acumed LLC, Hillsboro, OR (US)

( * ) Notice: Subject to any disclaimer, the term of this patent is extended or adjusted under 35 U.S.C. 154(b) by 456 days.

(21) Appl. No.: 12/616,054

(22) Filed: Nov. 10, 2009

(65) Prior Publication Data

US 2010/0121390 A1 May 13, 2010

Related U.S. Application Data

(60) Provisional application No. 61/112,878, filed on Nov. 10, 2008.

(51) Int. Cl.
*A61F 2/42* (2006.01)
(52) U.S. Cl. ............... 623/21.12; 623/21.11; 606/86 R
(58) Field of Classification Search ..... 623/21.11–21.14
See application file for complete search history.

(56) References Cited

U.S. PATENT DOCUMENTS

| | | | |
|---|---|---|---|
| 5,108,444 A | 4/1992 | Branemark |
| 5,358,529 A | 10/1994 | Davidson |
| 5,782,926 A | 7/1998 | Lamprecht |
| 5,879,395 A | 3/1999 | Tornier et al. |
| 5,938,699 A | 8/1999 | Campbell |
| 5,951,604 A | 9/1999 | Scheker |
| 6,379,387 B1 | 4/2002 | Tornier |
| 6,814,757 B2 | 11/2004 | Kopylov et al. |
| 6,945,976 B2 | 9/2005 | Ball et al. |
| 6,969,407 B2 | 11/2005 | Klotz et al. |
| 7,160,331 B2 | 1/2007 | Cooney, III et al. |
| 2004/0186580 A1 | 9/2004 | Steinmann |
| 2005/0049710 A1 | 3/2005 | O'Driscoll et al. |
| 2006/0004378 A1 | 1/2006 | Raines, Jr. et al. |
| 2007/0198095 A1 | 8/2007 | VanDer Muelen et al. |
| 2008/0249631 A1 | 10/2008 | Hassler et al. |

FOREIGN PATENT DOCUMENTS

| | | |
|---|---|---|
| FR | 2660856 A1 | 10/1991 |
| GB | 2269752 A | 2/1994 |

OTHER PUBLICATIONS

Bowers, William H., Distal radioulnar joint arthroplasty: The hemiresection-interposition technique. The Journal of Hand Surgery, vol. 10A, No. 2, 169-178 (1985).
Bowers, William H., Hemiresection Interposition Technique (HIT) Arthroplasty of the Distal Radioulnar Joint 303-318 in Master Techniques in Orthopaedic Surgery, The Wrist, Lippincott Williams & Wilkins: Boston (Richard H. Gelberman, ed., 1994).
Cooney III, William P. and Richard A. Berger, The Distal Radioulnar Joint 226-243 in Joint Replacement Arthroplasty, Churchill Livingstone: Philadelphia (Bernard F. Morrey, 3rd ed., 2003).
International Searching Authority, International Search Report, International Patent Application No. PCT/US2009/063926; search completion date: Dec. 30, 2009; date of mailing: Jan. 12, 2010.
International Searching Authority, Written Opinion of the International Searching Authority, International Patent Application No. PCT/US2009/063926; opinion completion date: Dec. 30, 2009; date of mailing: Jan. 12, 2010.
Darrow, Joseph C. et al., Distal ulnar recession for disorders of the distal radioulnar joint. The Journal of Hand Surgery, vol. 10A, No. 4, 482-491 (1985).

(Continued)

*Primary Examiner* — Andrew Yang
*Assistant Examiner* — Olivia C Chang
(74) *Attorney, Agent, or Firm* — Kolisch Hartwell, P.C.

(57) ABSTRACT

System, including methods, apparatus, and kits, for replacement of at least one surface region of a distal radioulnar joint using at least one prosthesis. In some embodiments, the system may provide restoration of normal, unconstrained biomechanics of the joint, which may preserve rotation and translation and ensure durability of the joint.

31 Claims, 13 Drawing Sheets

OTHER PUBLICATIONS

Gaebler, C. et al., Ulnar procedures for post-traumatic disorders of the distal radioulnar joint. Injury, International Journal of the Care of the Injured, vol. 34, 47-59 (2003).

Kleinman, William B., Salvage Procedures for the Distal End of the Ulna: There Is No Magic. The American Journal of Orthopedics 1-9 (2009).

Kopylov, Philippe and Magnus Tagil, Distal Radioulnar Joint Replacement. Techniques in Hand and Upper Extremity Surgery, vol. 11, No. 1, 109-114 (2007).

Scheker, Luis R. et al., Distal Ulnar Prosthetic Replacement. Advanced Techniques in the Management of Wrist Trauma, vol. 30, No. 2, 365-376 (2001).

Sheridan, Donald C. and Allen T. Bishop, The Distal Radioulnar Joint 347, 372-376 in Reconstructive Surgery of the Joints, vol. 1, Churchill Livingstone: New York (Bernard F. Morrey, 2nd ed., 1996).

U.S. Patent No. 6,814,757 File History, United States Patent and Trademark Office.

Wallwork, Nicholas A. and Gregory I. Bain, Sigmoid Notch Osteoplasty for Chronic Volar Instability of the Distal Radioulnar Joint: A Case Report. The Journal of Hand Surgery, vol. 26A, No. 3, 454-459 (2001).

Watson, H. Kirk et al., Matched distal ulnar resection. The Journal of Hand Surgery, vol. 11A, No. 6, 812-817 (1986).

U.K. Intellectual Property Office, Patents Act 1977—Examination Report under Section 18(3), U.K. Patent Application Serial No. GB1109656.7 (counterpart); report date: May 11, 2012.

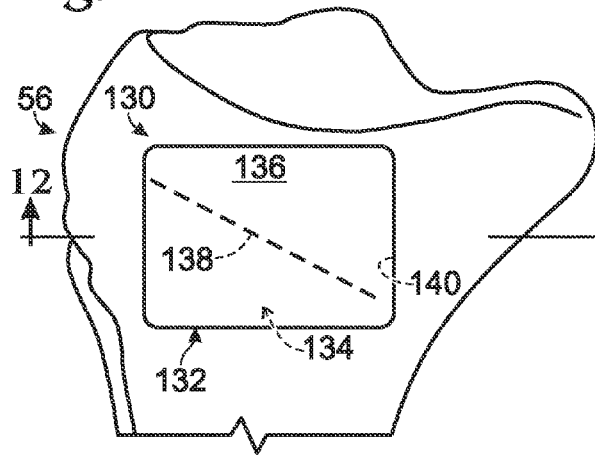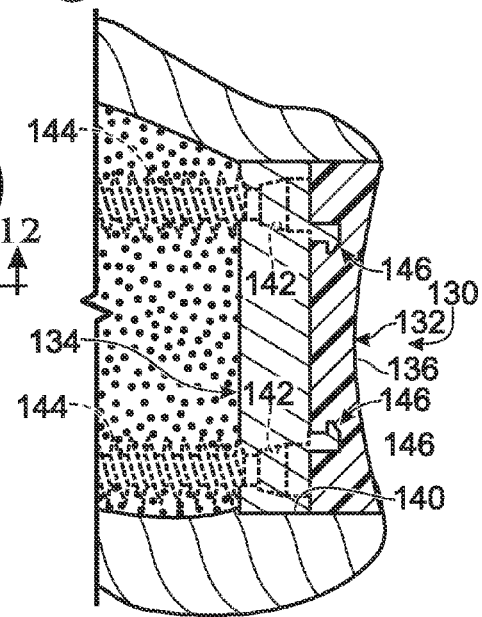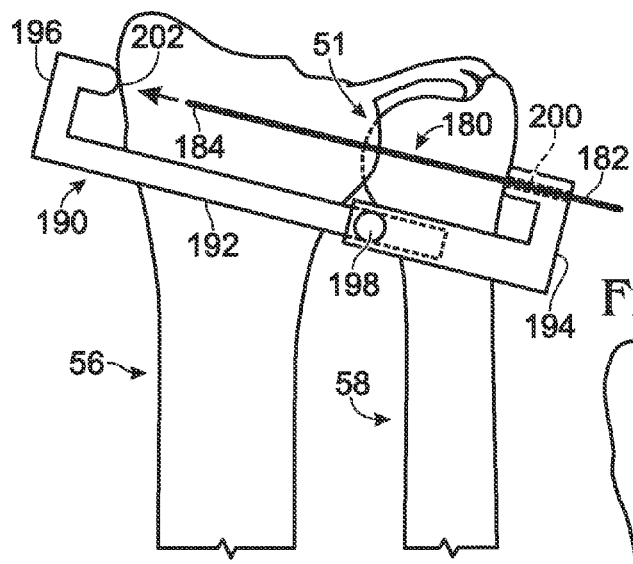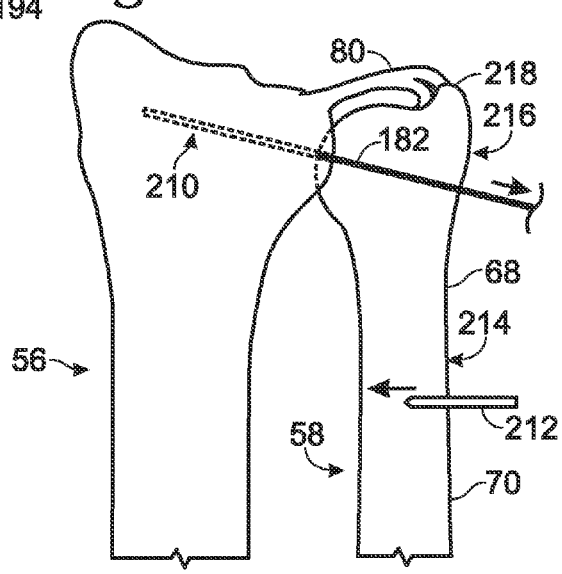

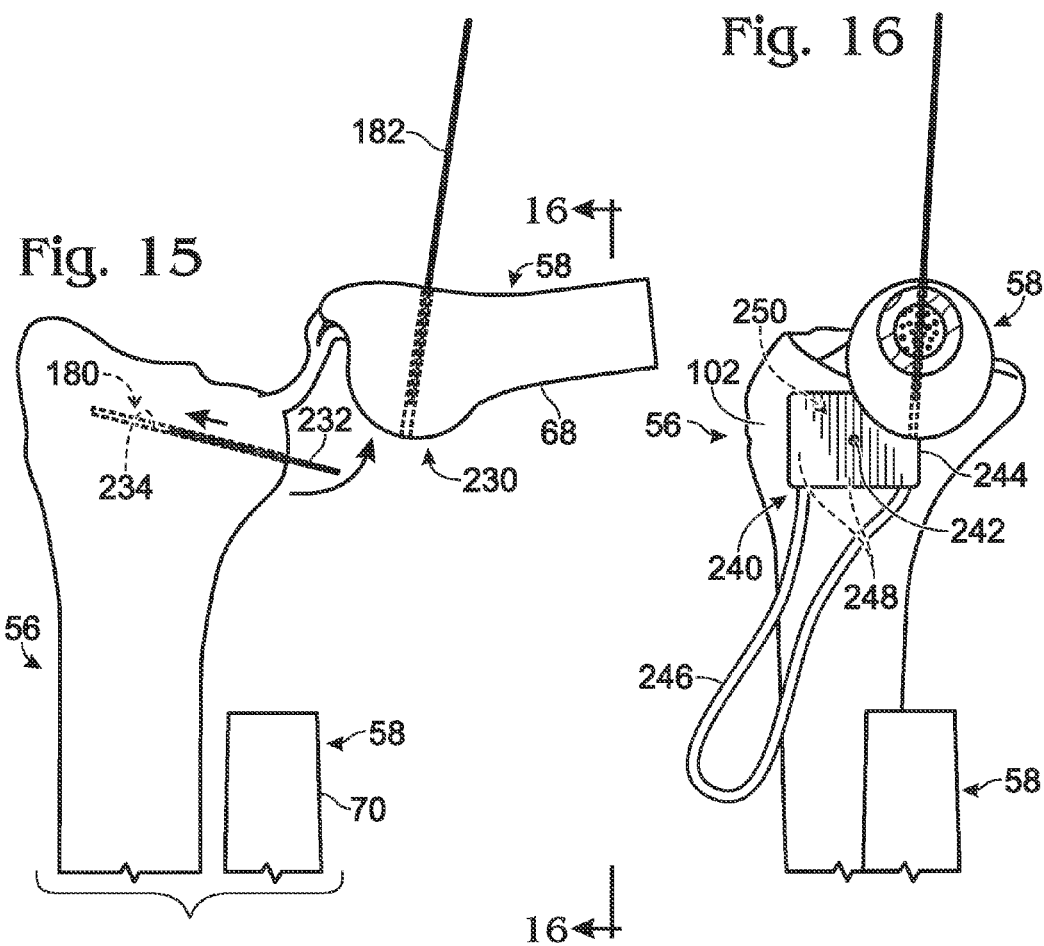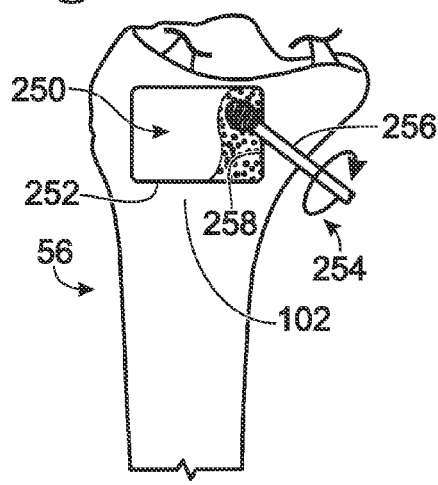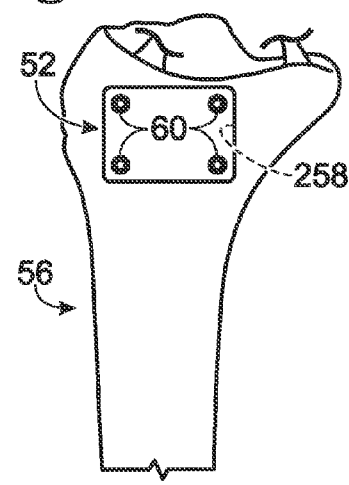

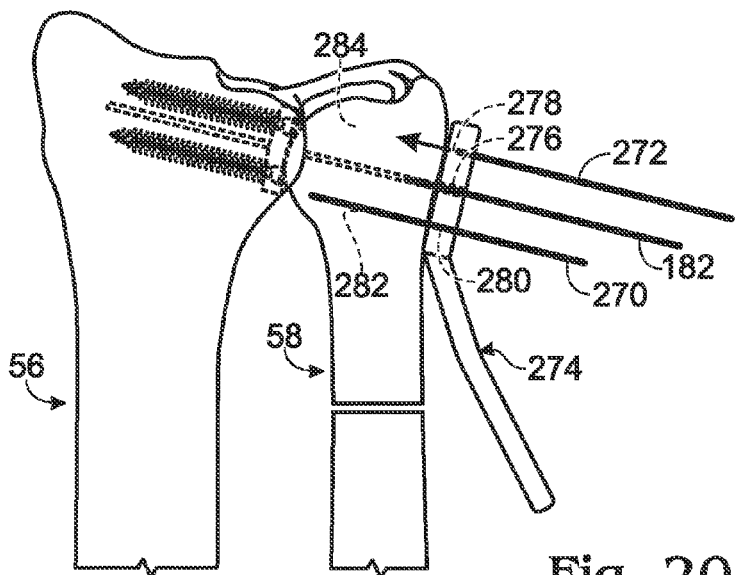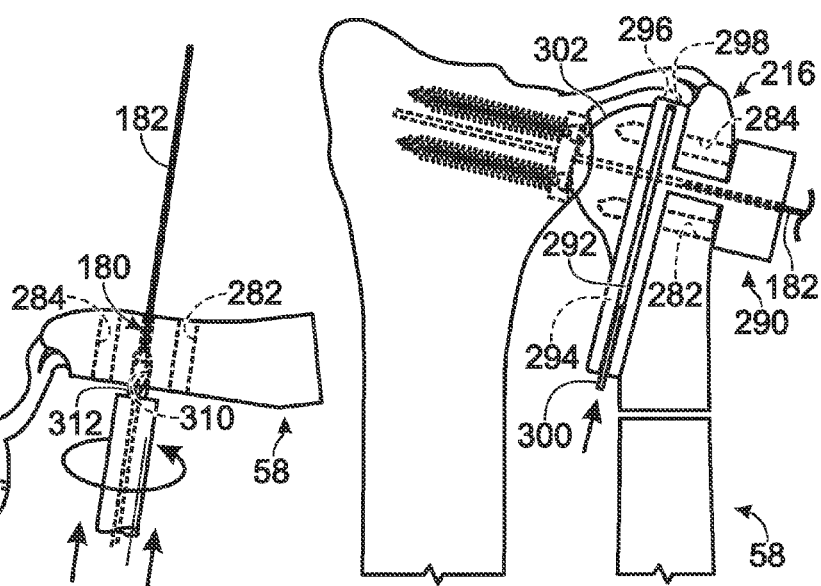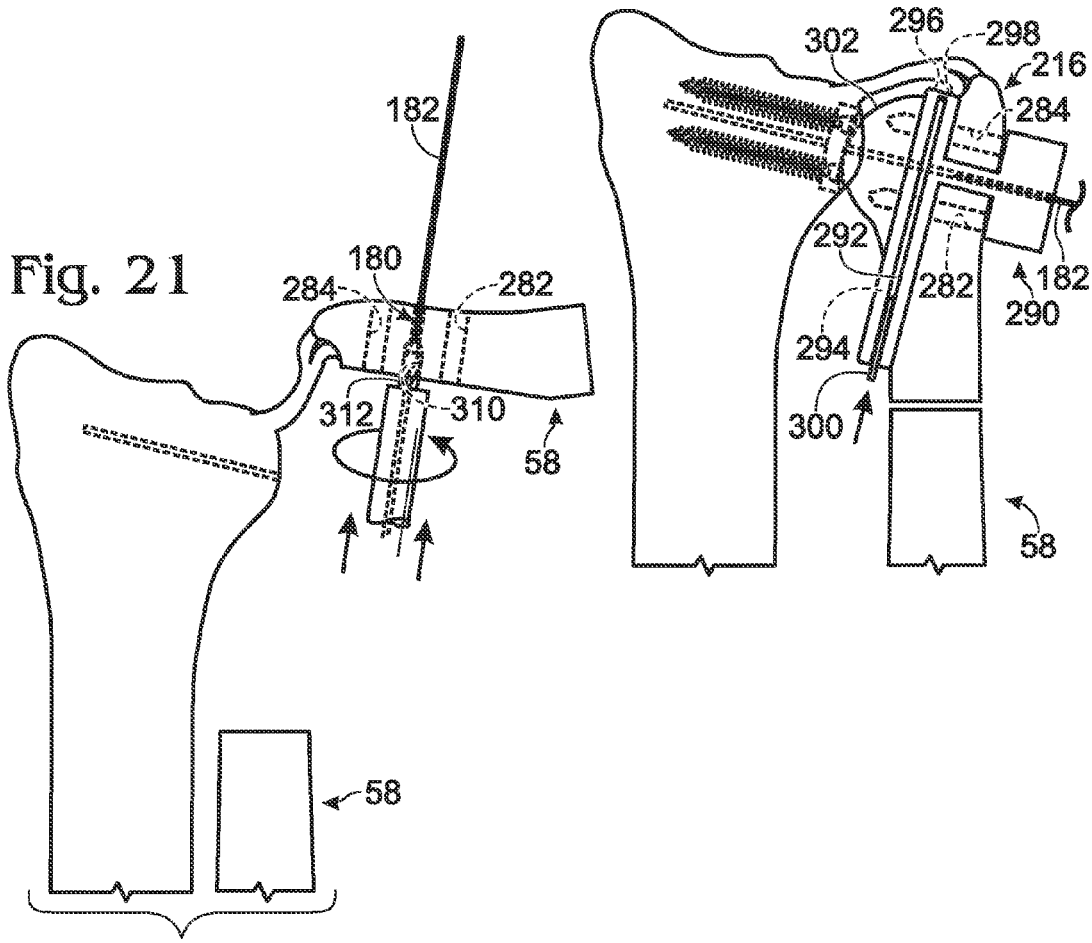

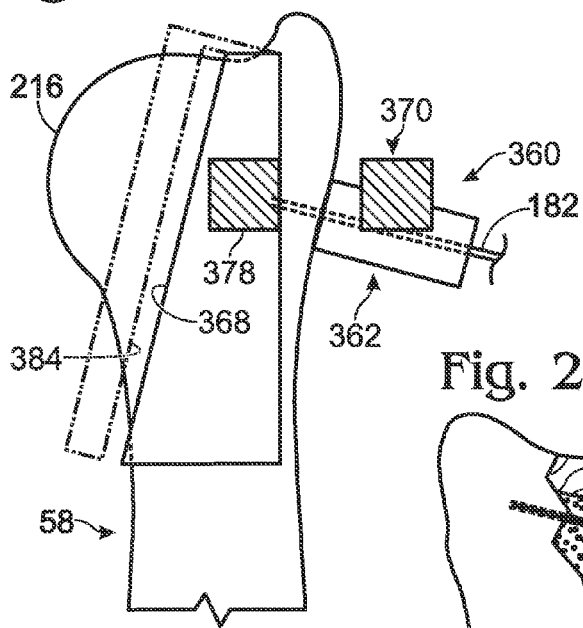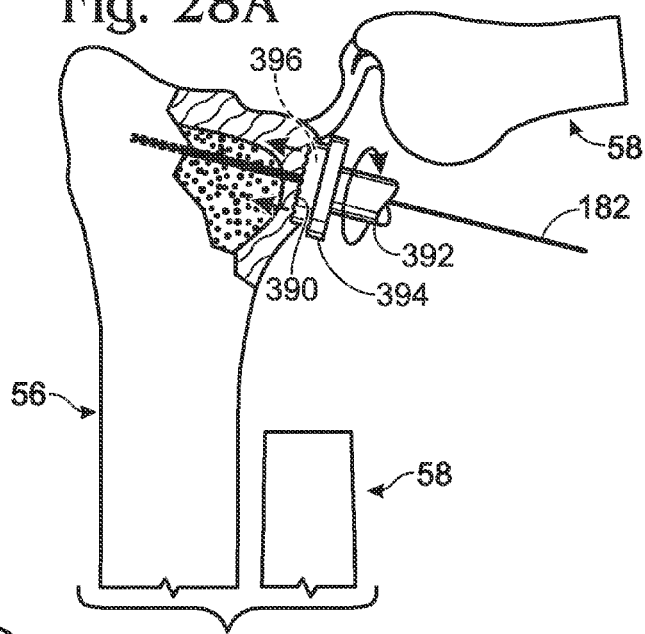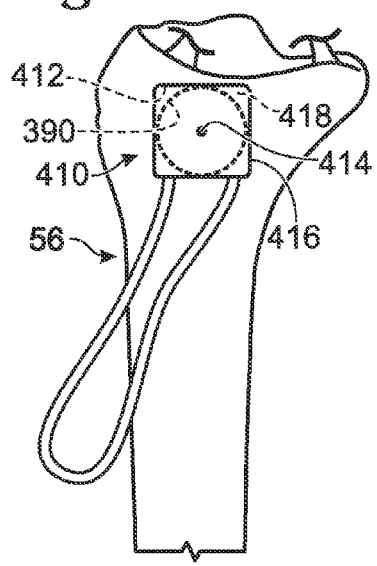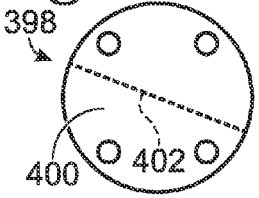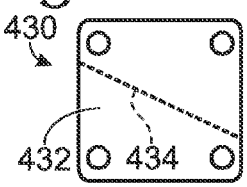

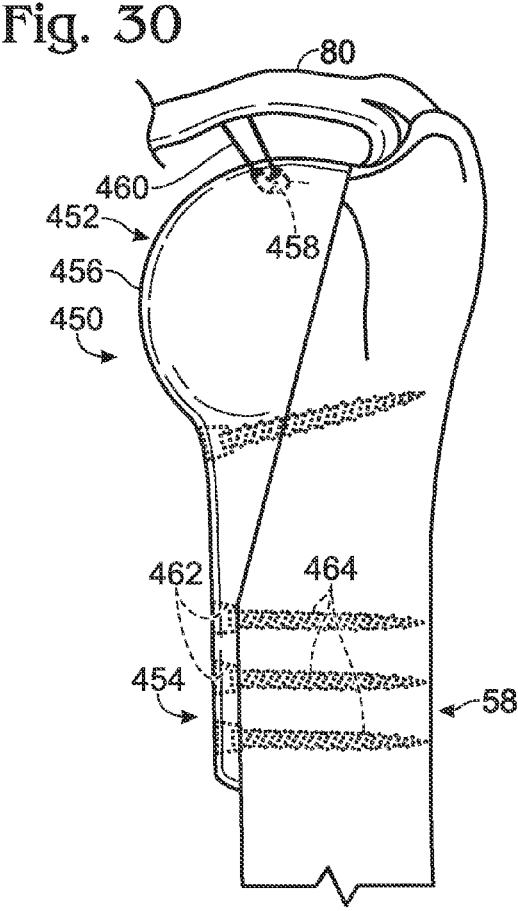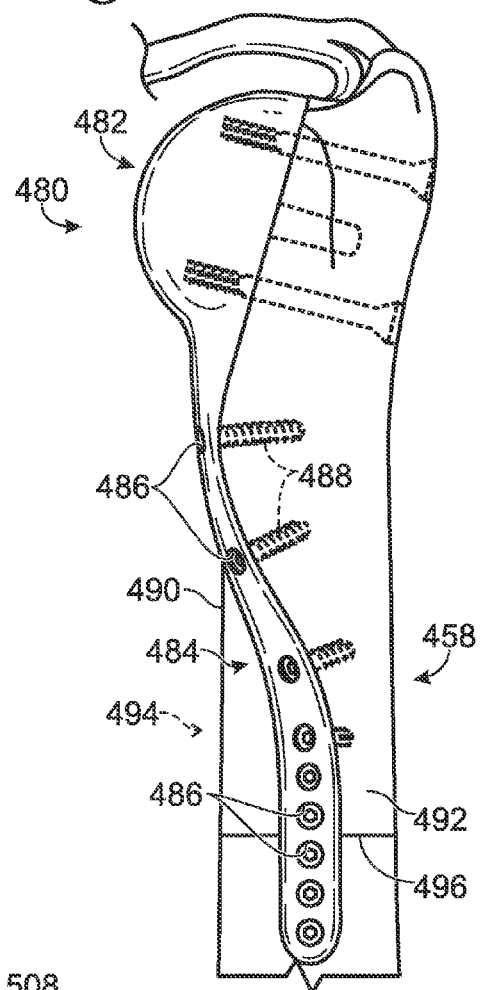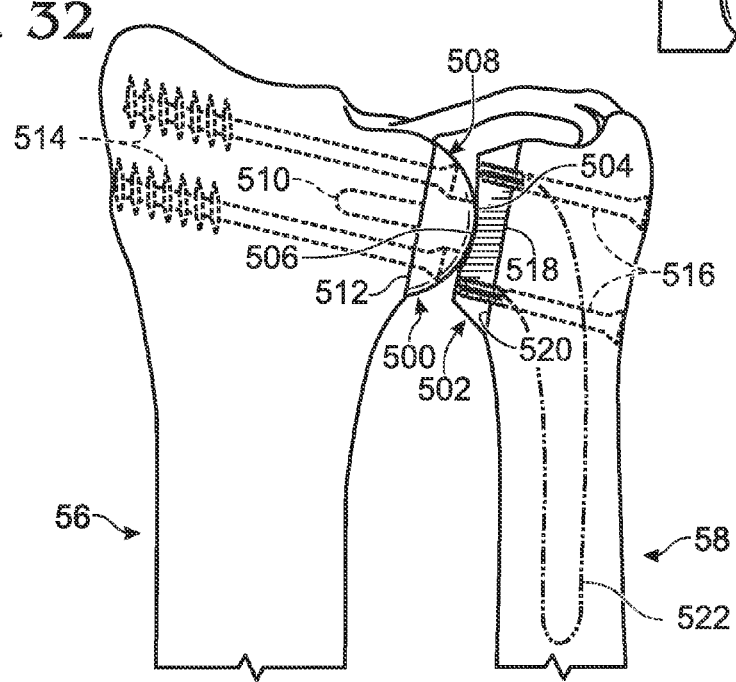

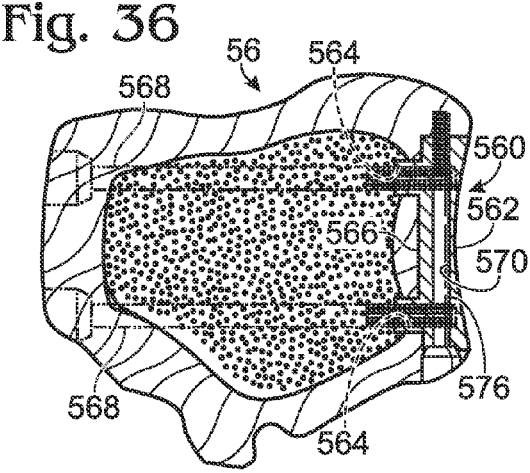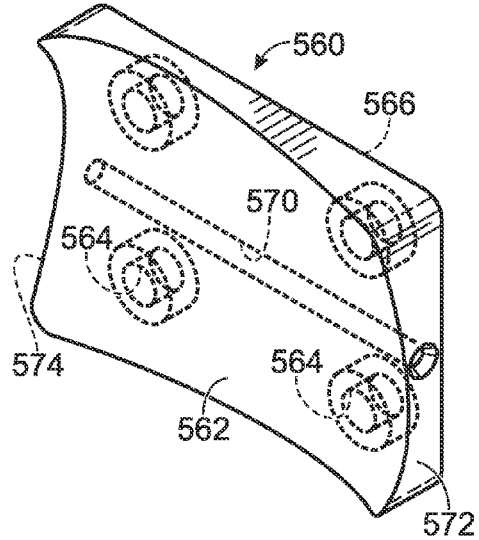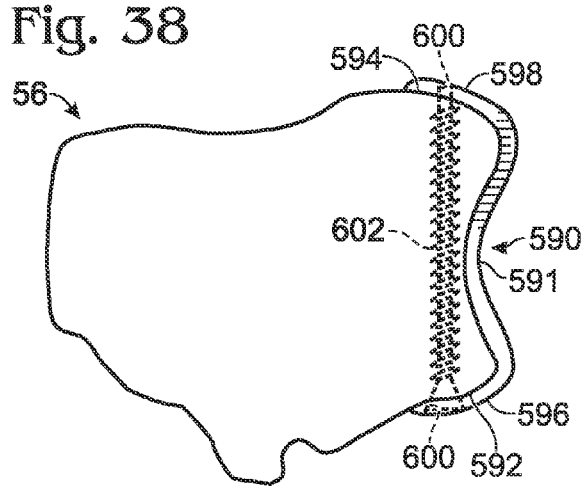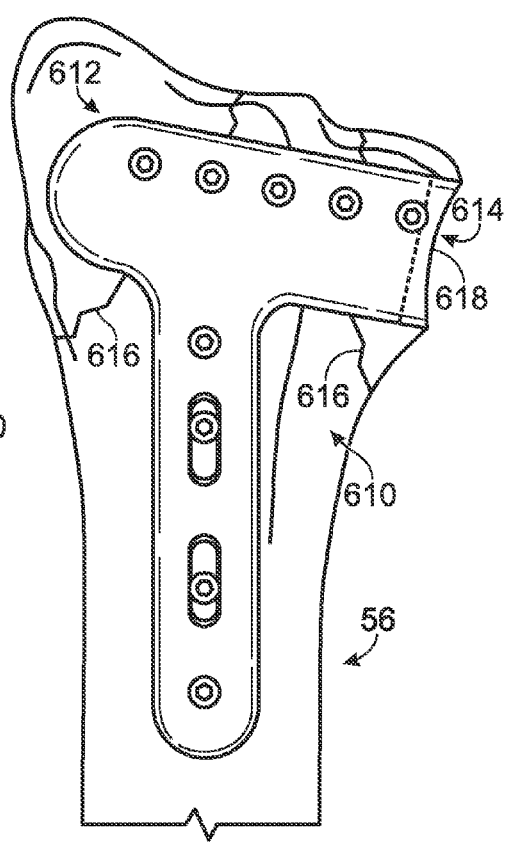

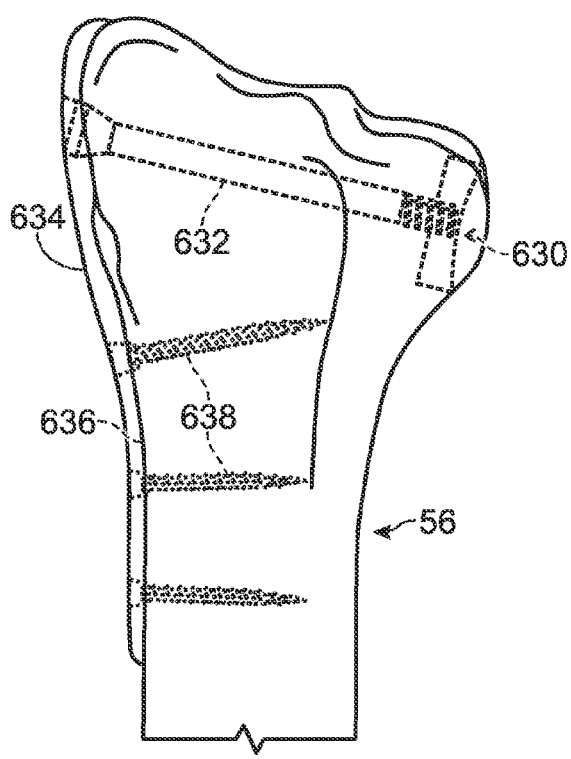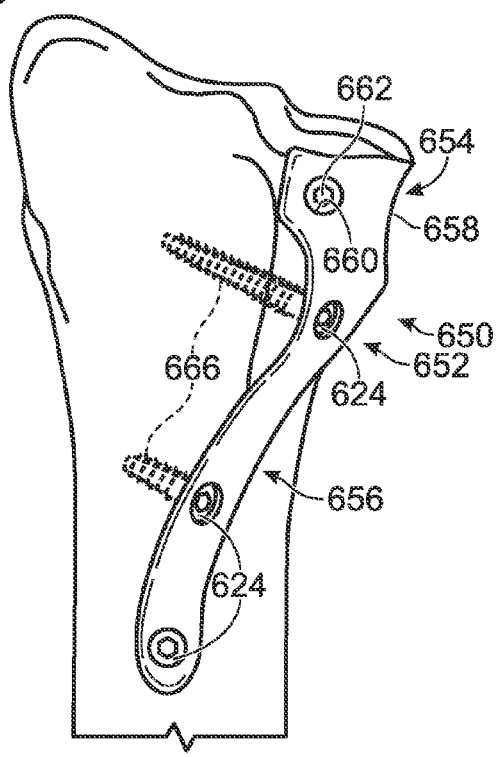

PARTIAL OR COMPLETE PROSTHETIC REPLACEMENT ARTHROPLASTY OF THE DISTAL RADIOULNAR JOINT

CROSS-REFERENCE TO PRIORITY APPLICATION

This application claims priority under 35 U.S.C. §119(e) to U.S. Provisional Patent Application Ser. No. 61/112,878, filed Nov. 10, 2008, which is incorporated herein by reference in its entirety for all purposes.

INTRODUCTION

The distal radioulnar joint (DRUJ) is a pivot joint formed in the wrist at the distal junction of the forearm bones, namely, the radius and the ulna. The joint is created by articulation between a lateral surface region of the distal ulnar head and a medial surface region of the radial sigmoid fossa. This articulation is important for integration of forearm-wrist-hand function, efficient supination and pronation of the wrist, and stability of the wrist under load.

The DRUJ may be damaged through gradual degeneration (e.g., rheumatoid arthritis) or traumatic injury, among others. The damaged DRUJ may become unstable, which may result in subluxation (partial dislocation) or dislocation, and acute pain. Most significantly, the damaged DRUJ almost invariably causes chronic pain to the afflicted individual.

Various surgical approaches have been developed over the past century to treat DRUJ instability and chronic pain. For example, in the Darrach procedure, the distal head of the ulna is resected completely, thereby eliminating the ulnar side of the joint. The Bowers procedure takes a more conservative approach to a similar goal, by resecting only a lateral portion of the distal ulnar head. As another example, the Sauvé-Kapandji procedure excises a segment of the ulna proximal to the distal ulnar head, and fixes the remaining ulnar head fragment to the distal radius with fasteners. However, none of these procedures is satisfactory because DRUJ function is abolished.

Implants also have been developed more recently for repair of the DRUJ, in an attempt to reduce DRUJ instability and pain without complete loss of DRUJ function. However, the design of these implants has been constrained, and their use hampered, by the surgical inaccessibility of the DRUJ. For example, installation of some of the implants involves complete removal of the end of the radius and/or ulna, which compromises or removes key ligaments (i.e., the triangular fibrocartilage complex (TFC)) involved in holding the DRUJ together. Others of the implants are designed to be implanted with minimal ligament damage, but may be difficult or impossible to install as intended, under actual surgical conditions. In any event, none of the implants sufficiently restores or reproduces the biomechanics of the DRUJ.

Thus, there is a need for more efficient procedures to access the DRUJ for repair without excessive damage to bone and soft tissue. Also, there is a need for improved DRUJ implants.

SUMMARY

The present disclosure provides a system, including methods, apparatus, and kits, for replacement of at least one surface region of a distal radioulnar joint using at least one prosthesis. In some embodiments, the system may provide restoration of normal, unconstrained biomechanics of the joint, which may preserve rotation and translation and ensure durability of the joint.

BRIEF DESCRIPTION OF THE DRAWINGS

FIG. 11 is a medial view of a distal radius bearing another exemplary radial prosthesis that replaces the radial portion of a distal radioulnar joint, in accordance with aspects of the present disclosure.

FIG. 12 is a fragmentary, sectional view of the radius and radial prosthesis of FIG. 11, taken generally along line 12-12 of FIG. 11.

FIGS. 13-22 are exemplary configurations that may be produced during performance of a method of replacing at least one surface region of a distal radioulnar joint with a prosthetic surface region, in accordance with aspects of the present disclosure.

FIG. 27 is a sectional view of the cutting guide of FIG. 26, taken generally along line 27-27 of FIG. 26 toward the ulna.

FIGS. 28A and 29A are other exemplary configurations that may be produced during performance of a method of replacing at least one surface region of a distal radioulnar joint with a prosthetic surface region, in accordance with aspects of the present disclosure.

FIGS. 28B and 29B are plan views of exemplary radial head prostheses that may be implanted using the configurations produced in FIGS. 28A and 29A, respectively, in accordance with aspects of the present disclosure.

FIG. 30 is a dorsal view of a distal ulna with the seat and pole of the distal ulnar head resected and replaced by another exemplary ulnar prosthesis, in accordance with aspects of the present disclosure.

FIG. 31 is a dorsal view of a distal ulna that has been osteotomized, with the seat and pole of the distal ulnar head resected and replaced by an exemplary ulnar prosthesis that also fixes the osteotomized ulna, in accordance with aspects of the present disclosure.

FIG. 32 is a dorsal view of a distal radius and ulna of a right forearm after total replacement of the distal radioulnar joint with "reverse" radial and ulnar prostheses constructed and installed in accordance with aspects of the present disclosure.

FIG. 36 is a sectional view of the distal radius and radial prosthesis of FIG. 35, taken generally along line 36-36 of FIG. 35.

FIG. 37 is an isometric view of the radial prosthesis of FIG. 35 taken in the absence of fasteners and bone.

FIG. 38 is a distal view of a radius bearing an exemplary radial prosthesis that mounts over the radial portion of a distal radioulnar joint, in accordance with aspects of the present disclosure.

FIG. 39 is a dorsal view of a fractured distal radius bearing an exemplary bone plate that also supplies a prosthetic surface for the radial portion of a distal radioulnar joint, in accordance with aspects of present disclosure.

FIG. 40 is a dorsal view of a distal radius bearing an exemplary radial prosthesis secured in a retrograde direction by a fastener extending through a plate from a lateral side of the distal radius, in accordance with aspects of the present disclosure.

FIG. 41 is a dorsal view of a distal radius bearing still yet another exemplary radial prosthesis that replaces the radial portion of a distal radioulnar joint, in accordance with aspects of the present disclosure.

DETAILED DESCRIPTION

Figure 1:
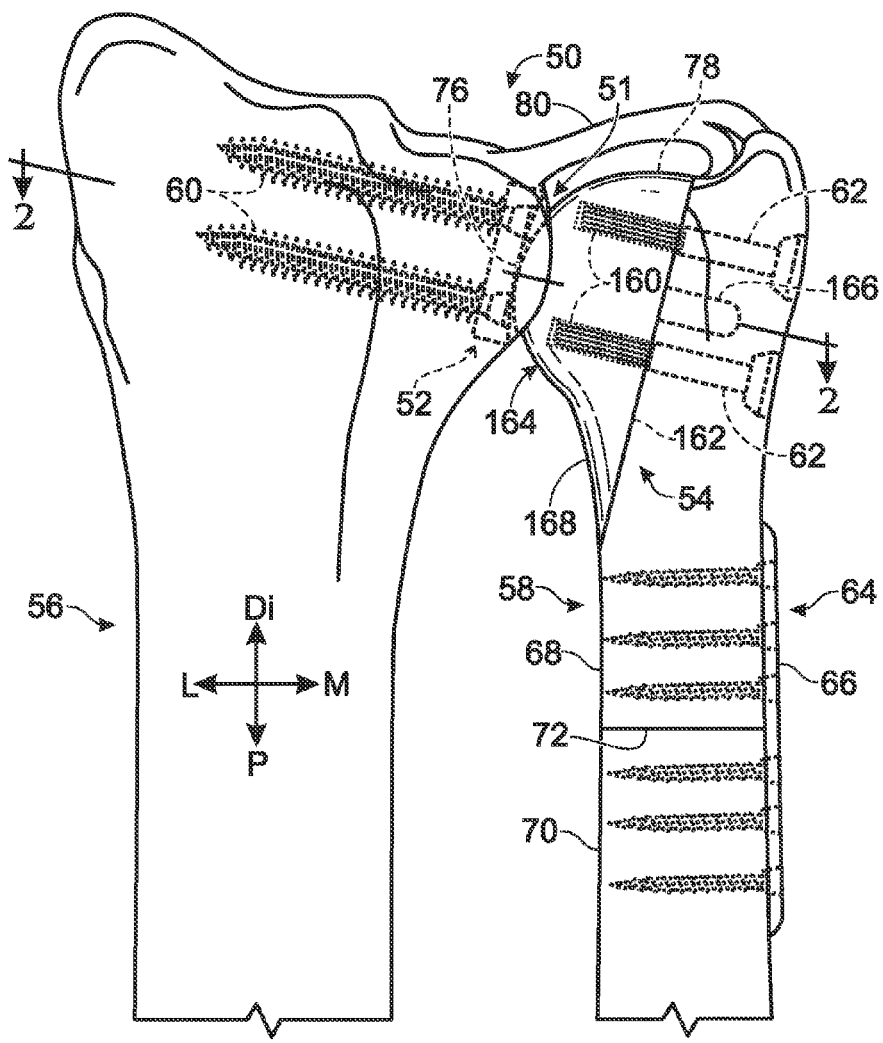
FIG. 1 is a dorsal view of a distal radius and ulna of a right forearm after total replacement of the distal radioulnar joint with exemplary radial and ulnar prostheses that are constructed and implanted in accordance with aspects of the present disclosure.

The present disclosure provides a system, including methods, apparatus, and kits, for replacement of at least one surface region of a distal radioulnar joint using at least one prosthesis. In some embodiments, the system may provide restoration of normal, unconstrained biomechanics of the joint, which may preserve rotation and translation and ensure durability of the joint.

A method is provided of repairing a distal radioulnar joint formed by a radius and an ulna. A shaft region of the ulna may be cut through to form a proximal ulnar fragment and a distal ulnar fragment. The distal ulnar fragment may be moved away from the proximal ulnar fragment to a spaced configuration, such as by pivoting the distal ulnar fragment to a reflected configuration. Bone may be removed from a sigmoid fossa region of the radius, from a generally laterally facing region of the distal ulnar head, or from both, while the distal ulnar fragment is in the spaced configuration. A radial prosthesis, an ulnar prosthesis, or both, may be installed in place of bone that has been removed, to replace at least one surface region of the distal radioulnar joint. The proximal and distal ulnar fragments may be fixed relative to each other.

A method is provided of repairing at least a radial side of a distal radioulnar joint formed by a radius and an ulna. A radial prosthesis may be selected. The radial prosthesis may include an outer surface forming a groove. The radial prosthesis may be attached to the radius such that the outer surface replaces a radial surface region of the distal radioulnar joint.

A method is provided of repairing a distal radioulnar joint formed by a radius and an ulna. An elongate guide member may be placed into the radius and ulna such that the guide member defines a linear datum extending through the distal radioulnar joint. Bone may be removed, using the linear datum as a reference, from a sigmoid fossa region of the radius and from a generally laterally facing region of the distal ulnar head. A radial prosthesis and an ulnar prosthesis may be installed to replace respective radial and ulnar surface regions of the distal radioulnar joint.

A kit is provided for repairing a distal radioulnar joint formed by a radius and an ulna. The kit may comprise at least one prosthesis selected from a radial prosthesis, an ulnar prosthesis, or both, to replace at least one surface region of the distal radioulnar joint. The kit also may comprise a bone plate to fix proximal and distal ulnar fragments relative to each other.

A device is provided for repairing a distal radioulnar joint formed by a radius and an ulna. The device may comprise a radial prosthesis including a dished outer surface forming a groove.

The system disclosed herein may have substantial advantages over other approaches to DRUJ repair. For example, the system may provide better access to DRUJ surfaces, which may enable more conservative and/or accurate removal of bone, and/or better attachment and/or more precise placement of prostheses, among others. The system also or alternatively may offer more accurate restoration of normal (anatomical), unconstrained biomechanics of the joint.

Further aspects of the present disclosure are presented in the following sections: (I) system for replacement of the distal radioulnar joint, (II) method of surface replacement of a distal radioulnar joint, (III) composition of implants, (IV) kits, and (V) examples.

I. System for Replacement of the Distal Radioulnar Joint

FIG. 1 shows selected components of an exemplary system 50 for replacement of one or more surface regions of a distal radioulnar joint (DRUJ) 51 of a forearm. System 50 may include a radial prosthesis 52 and/or an ulnar prosthesis 54 attached, respectively, to a radius 56 and/or an ulna 58 using, for example, a plurality of fasteners 60, 62. The prostheses are viewed in FIG. 1 from the dorsal side of a right forearm; exemplary anatomical axes, namely a medial-lateral axis (M-L) and a proximal-distal axis (P-Di) are indicated. System 50 also may include a fixation device 64, such as a bone plate 66, to fix distal and proximal ulnar fragments 68, 70 in axial alignment with one another. The ulnar fragments may, for example, result from an osteotomy that forms a transverse cut 72 through a shaft region of the ulna, to enable installation of prostheses 52, 54.

Each prosthesis 52, 54 may be shaped and positioned to provide at least a replacement surface region for a radial articulation surface or an ulnar articulation surface of distal radioulnar joint 51. For example, the radial prosthesis may replace at least a portion of the sigmoid fossa of the radius. Also, or alternatively, the ulnar prosthesis may replace at least a lateral portion of the head of the distal radius. In some embodiments, the ulnar prosthesis may replace an ulnar lateral surface region 76, also termed a seat, that faces and articulates with the sigmoid fossa, and also may replace an ulnar end surface region 78, termed a pole, disposed laterally to the ulnar fovea and facing generally distally from the ulna. In any event, the radial prosthesis and/or ulnar prosthesis may be installed without disturbing attachment of the triangular fibrocartilage complex (TFC) 80 to radius 56 or ulna 58.

Figure 2:
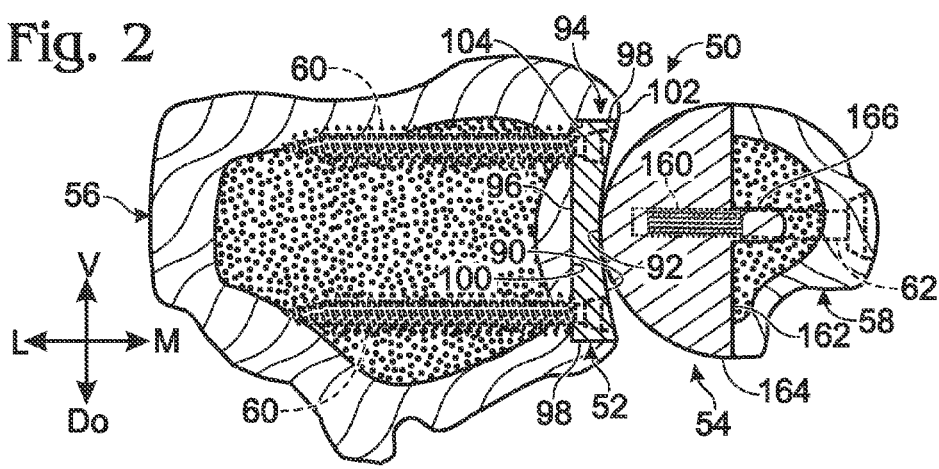
FIG. 2 is a sectional view of the distal radius and ulna and corresponding prostheses of FIG. 1 taken generally along line 2-2 of FIG. 1.

FIG. 2 shows a sectional view of system 50 taken generally through a proximal-distal plane of radius 56 and ulna 58.

Exemplary anatomical axes, namely a medial-lateral axis (M-L) and a dorsal-volar axis (Do-V) are indicated. Radial prosthesis 52 and ulnar prosthesis 54 may furnish respective outer surfaces 90, 92 that face and movably contact one another to function as prosthetic replacement surfaces in the distal radioulnar joint. In the present example, both radial and ulnar sides of the distal radioulnar joint have been replaced with prosthetic joint surfaces in a total arthroplasty. However, in other examples, only the radial side or only the ulnar side may be replaced with a radial prosthesis or an ulnar prosthesis, respectively, in a hemiarthroplasty. In other words, the radial (or ulnar) prosthesis after installation may articulate in the distal radioulnar joint with a replacement articulation surface or with a natural articulation surface.

A. Radial Prosthesis

Figure 3:
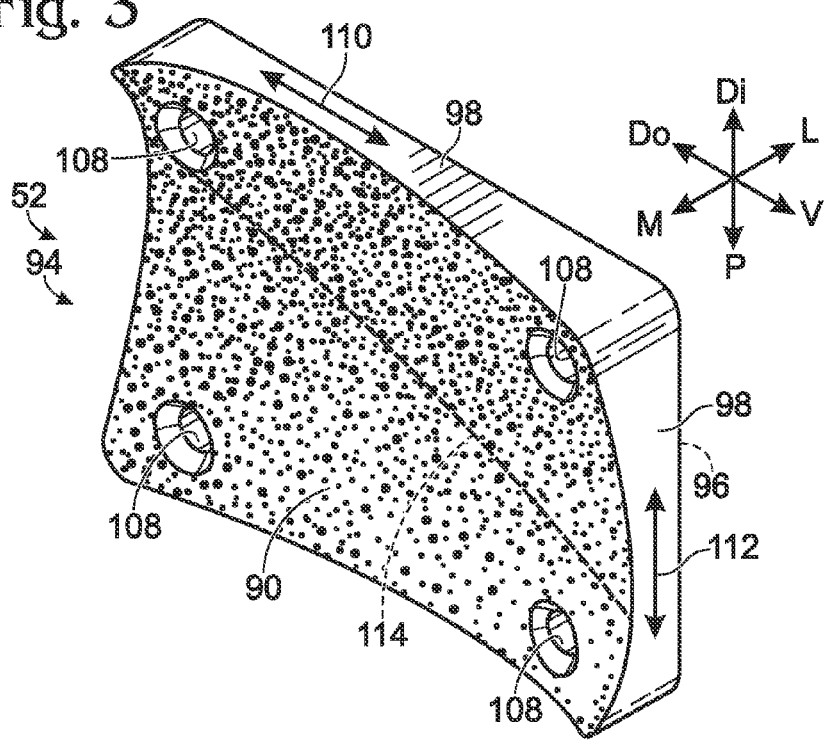
FIG. 3 is an isometric view of the radial prosthesis of FIG. 1, taken generally from the articulating side of the prosthesis in the absence of bone and fasteners, and with stippling (speckles) added to the drawing as an artistic representation of surface contour.
Figure 4:
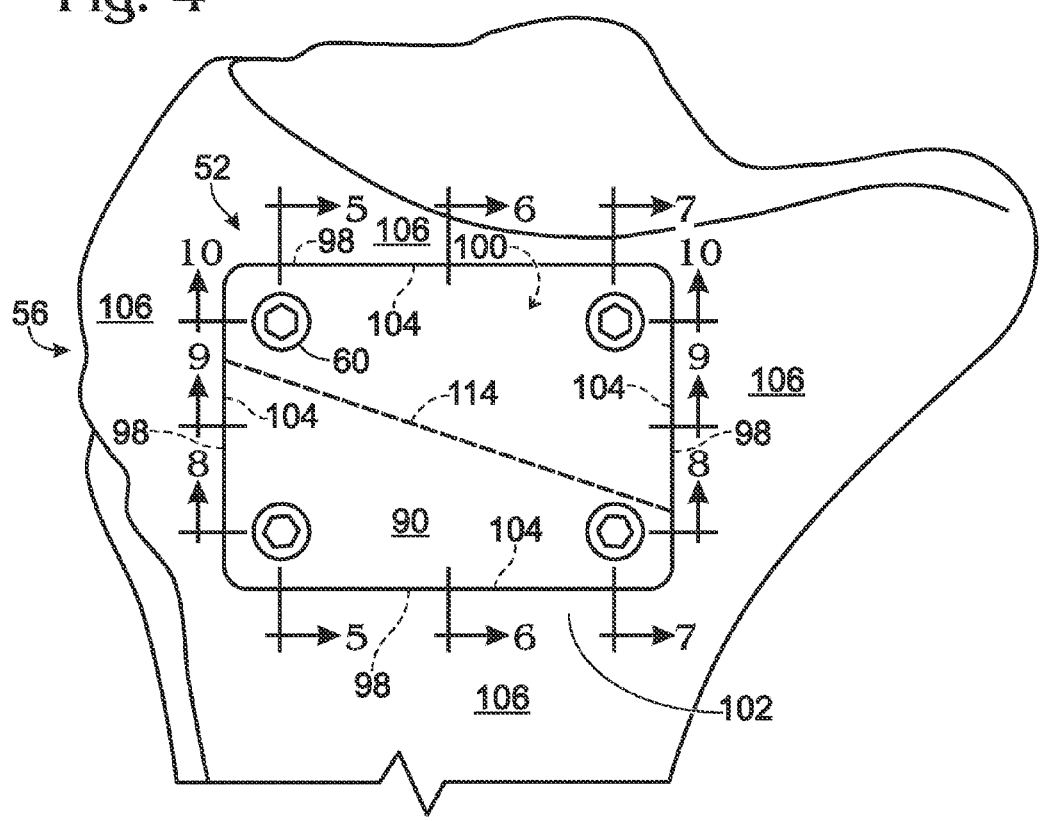
FIG. 4 is a medial view of the distal radius and radial prosthesis of FIG. 1, taken toward the sigmoid fossa of the radius in the absence of the ulna and associated ligaments.
Figure 5:
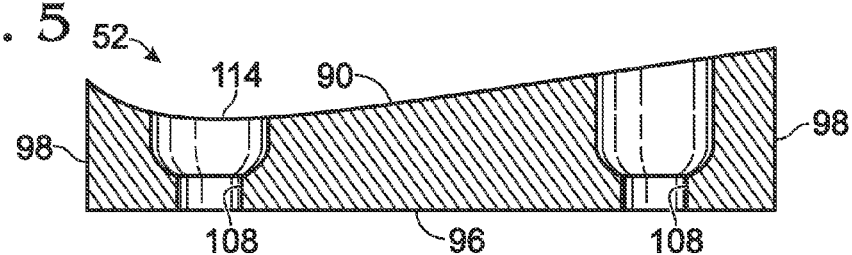
FIGS. 5-10 are a series of sectional views of the radial prosthesis of FIG. 1, taken generally along lines 5-5, 6-6, 7-7, 8-8, 9-9, and 10-10, respectively, of FIG. 4 and depicted in the absence of bone and fasteners.
Figure 6:
Figure 7:
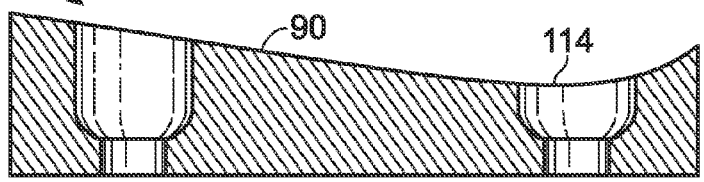
Figure 8:
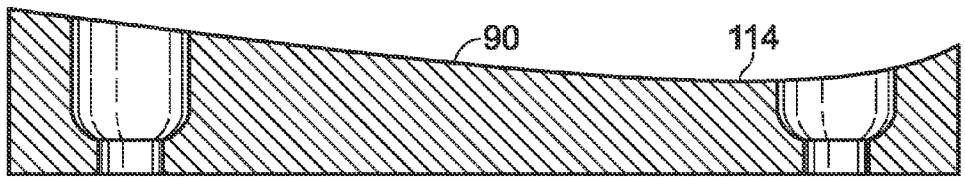
Figure 9:
Figure 10:
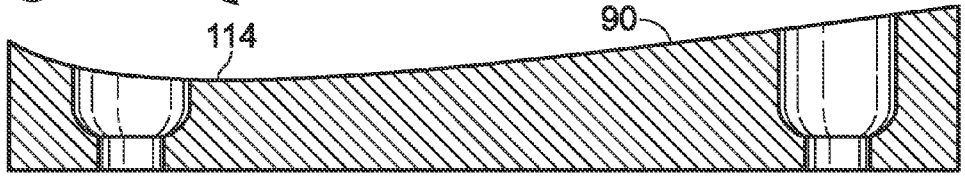

FIGS. 2-4 show additional aspects of radial prosthesis 52. The radial prosthesis may be structured as a plate 94, which may (or may not) be monolithic. The prosthesis may have an inner surface 96 that opposes outer surface 90. The inner surface may be flat (i.e., at least substantially planar) or may be curved (e.g., convexly), among others. The inner surface may be free of projections (e.g., integral projections) or may have at least one integral stem and/or ridge projecting from the inner surface, among others.

Outer surface 90 and inner surface 96 may be separated by side surfaces 98, which may form a perimeter of the prosthesis. The side surfaces may be at least substantially flat, to form linear profiles (e.g., see FIG. 4), or may be curvilinear, to form curved profiles. In any event, the corners where side surfaces 98 meet may be rounded, as shown here, may be sharp, or may be absent (e.g., in a circular configuration). The side surfaces may be oriented at least substantially orthogonally to inner surface 96. At least one pair of opposing side surfaces 98 may define respective long axes that are parallel (or oblique) to each other. Thus, in some embodiments, the radial prosthesis may have four side surfaces to create a quadrilateral shape that is at least generally rectangular (i.e., elongate or square) or trapezoidal, among others. In other embodiments, the radial prosthesis may be circular, elliptical, polygonal with more or fewer than four sides, or the like.

The radial prosthesis may be structured to be inlaid (inset) in bone, as shown in FIGS. 1, 2, and 4. In other words, the radial prosthesis may be received partially or at least substantially completely in a cavity 100 formed in sigmoid fossa 102, such that the prosthesis is circumscribed by walls 104 of the cavity, with side surfaces 98 facing walls 104 (see FIGS. 2 and 4). When installed, outer surface 90 may (or may not) be at least substantially flush with surrounding surface regions 106 of the radius, where prosthetic outer surface 90 meets bone surface regions 106 (see FIG. 4).

The radial prosthesis may have any suitable dimensions. For example, the radial prosthesis may have a length that is greater than or equal to its width. The thickness of the radial prosthesis may be substantially less than the length and/or width, such as no more than about one-half the length and/or width. The thickness may vary across the prosthesis, as described below, or may be constant, if the inner and outer surfaces have complementary shapes. In exemplary embodiments, intended for illustration only, the radial prosthesis may be approximately three-quarters of an inch (19 mm) wide by five-eighths of an inch (16 mm) long by one-quarter of an inch (6.3 mm) deep in a typical adult patient.

The radial prosthesis (and/or ulnar prosthesis) may have any suitable type, number, and arrangement of apertures 108 (see FIG. 3). For example, radial prosthesis 52 may define an aperture near each corner. In any event, each aperture may be structured to receive a fastener, such as a bone screw. The aperture may be a through-hole, such as a through-hole that extends between inner and outer surfaces of the prosthesis or may not extend completely through the prosthesis (see below). The aperture may be a locking aperture, such as an internally threaded aperture that locks to the fastener by threaded engagement, or may be a compression/toggle aperture that receives a fastener without threaded engagement with the fastener. Thus, the aperture may predefine an axis for fastener placement or may permit fastener placement over a range of angles. In some embodiments, the radial prosthesis may include a combination of one or more locking apertures and one or more (nonlocking) compression/toggle apertures.

Fasteners 60 may be received in apertures 108 and advanced into bone through any suitable distance and in any suitable orientation (see FIGS. 2 and 4). Each fastener 60 may, for example, be a cancellous bone screw, with a prominent thread. The fastener may, for example, extend at least about one-third, one-half, or three-fourths of the distance across the radius (medial to lateral). At least a pair of fasteners 60 may extend parallel to one another, or may diverge or converge as they extend away from the prosthesis. Divergence or convergence of the pair of fasteners may be in a dorsal-volar direction, a medial-lateral direction, a proximal-distal direction, or any combination thereof. In some cases, a plurality of fasteners may diverge from one another as they extend from the radial prosthesis, to provide a splayed-out arrangement of fasteners, which may anchor the prosthesis more effectively to bone. In some embodiments, at least one fastener may approach and lock to the prosthesis in a retrograde direction (i.e., by placement of the fastener in a lateral to medial direction) or may be received via a side surface of the prosthesis from a volar or dorsal direction (e.g., see Section V).

FIGS. 3-10 show an exemplary shape for outer surface 90 of radial prosthesis 52. Surface 90 is depicted as stippled in FIG. 3 as a teaching aid, to facilitate understanding of the surface's three-dimensional contours. The outer surface is generally very smooth, even polished, to encourage fluid movement at the repaired joint.

Outer surface 90 may be dished. In other words, the outer surface may have concave curvature in each of two directions that are at least generally orthogonal to one another. In some embodiments, the outer surface may be formed with compound curvature, which can be defined with respect to the characteristic length and width axes 110, 112 of the prosthesis and/or with respect to anatomical axes when the prosthesis is installed. The outer surface may have a first concave curvature centered generally about an axis parallel to width axis 112 of the prosthesis and/or about an axis parallel to a proximal to distal axis (labeled as P-Di in FIG. 3), such that the first curvature extends generally lengthwise in the prosthesis and/or generally in a dorsal to volar direction when the radial prosthesis is attached operatively to the radius. Outer surface 90 also may have a second concave curvature centered generally about an axis that is parallel or oblique to length axis 110 of the prosthesis and/or this is parallel or oblique to one or more dorsal-volar axes (labeled as Do-V in FIG. 3), such that the second curvature extends generally widthwise (or obliquely thereto) in the prosthesis and/or in a proximal to distal direction (or obliquely thereto) when the radial prosthesis is attached operatively to the radius.

The compound curvature of outer surface 90 may form a groove 114, which may be a shallow, gently rounded trough. The groove is marked by a dashed line in FIGS. 3 and 4 and is visible in the sectional views of prosthesis 52 presented in FIGS. 5-10. The groove may be oriented parallel to length axis 110, and/or generally parallel to a dorsal-volar axis defined anatomically when installed. Alternatively, the groove may be oriented obliquely to length axis 110, as shown in FIGS. 3-10. For example, groove 114 may extend at an oblique angle of about 5-25, 10-20, or about 15 degrees with respect to length axis 110 and/or with respect to a dorsal-volar axis defined anatomically when the prosthesis is installed (e.g., at an oblique angle from a more distal dorsal position to a more proximal volar position).

Groove 114 may represent the principal load-bearing axis of the distal radioulnar joint. Accordingly, the seat of the ulna (and/or the prosthetic seat provided by the ulnar prosthesis) may travel along the groove, by rotation and translation, generally from left to right in FIGS. 3 and 4, as the hand distal to the radius and ulna is moved from supination to pronation. Thus, if the groove is oriented obliquely, the proximal-distal position of the distal end of the ulna may change (e.g., by about 4-5 millimeters), as the seat of the ulna rotates and translates along the groove during movement between supination and pronation of the hand. Groove 114 thus may encourage prosthetic joint motion that reproduces the action of a natural distal radioulnar joint, for better restoration of joint function.

FIGS. 11 and 12 show respective medial and sectional views of distal radius 56 bearing another exemplary radial prosthesis 130 that replaces the radial portion of a distal radioulnar joint. Radial prosthesis 130 may have any combination of the features described elsewhere in the present disclosure for radial prostheses (e.g., radial prosthesis 52).

Radial prosthesis 130 may be a multi-piece device that includes a superficial face piece 132 (a front piece) and a base 134 (a back piece). The base may be anchored to bone and may serve as a bridge between bone and the face piece to connect the face piece to bone. The face piece and the base may be formed of the same or different materials. For example, the base may be formed of metal (e.g., titanium) and the face piece of plastic (e.g., ultra-high molecular weight polyethylene) or metal (e.g., cobalt-chrome), among others. Thus, the use of a multi-piece prosthesis provides more freedom in selection of materials. Other suitable materials for the base and face piece are described below in Section III.

Face piece 132 may have an outer surface 136 shaped to form a radial side of a distal radioulnar joint. For example, the face piece may define a groove 138 like that described above for radial prosthesis 52 (e.g., see FIG. 3). However, the face piece may have a continuous outer surface 136 that is not interrupted by apertures. Accordingly, the face piece may, for example, provide a less-irritating surface for articulation in the distal radioulnar joint after a hemiarthroplasty.

Base 134 may enable a fixed connection of face piece 132 to bone by forming a bridge between the face piece and bone. The base may be received in a cavity 140 formed in the sigmoid fossa of the radius, to engage bone. The base may be attached to the radius by any suitable mechanism(s). For example, the base may define one or more apertures 142 that receive threaded fasteners 144 to attach the base to bone. Alternatively, or in addition, the base may be secured to bone with an adhesive (e.g., bone cement), a press-fit (e.g., by forcing a stem of the base into an undersized bore in the radius), or a combination thereof, among others. After attachment to the radius, the base may be engaged with the face piece. For example, the base may receive the face piece in a snap-fit connection provided by at least generally complementary retention structure 146 formed on and/or in the outer surface of the base and on and/or in the inner surface of the face piece. In other embodiments, the face piece may extend over one or more side surfaces of the base when attached to the base. Rather than, or in addition to, a snap-fit connection, the face piece may be secured to the base via fasteners and/or an adhesive, among others.

B. Ulnar Prosthesis

FIGS. 1 and 2 show further aspects of ulnar prosthesis 54. The ulnar prosthesis may have any of the features described above for the radial prosthesis. For example, the ulnar prosthesis may be formed as one piece. Alternatively, the ulnar prosthesis may be a multi-piece construct, such as with an inner base and a discrete outer face piece, generally as described for radial prosthesis 130 (FIGS. 11 and 12). Also, the ulnar prosthesis may define one or more apertures that are through-holes or blind holes. For example, in the present illustration, the ulnar prosthesis defines a pair of internally threaded apertures 160 that lock to lag screws 62 at the leading ends thereof.

The ulnar prosthesis may include an inner surface 162 that generally opposes outer surface 92 (see FIGS. 1 and 2). The inner surface may be flat (predominantly in one plane), may be composed of at least two flat surfaces disposed at an acute, right, or obtuse angle with respect to one another, may be curved (e.g., spherical), or a combination thereof, among others.

The ulnar prosthesis (and/or the radial prosthesis) may be equipped with a body 164 that forms inner and outer surfaces 92, 162, and a stem 166 that projects from inner surface 162. The stem may be fixed to the body and may project orthogonally or obliquely from inner surface 162. The stem may be integral to the body or may be formed by a separate, discrete piece. The stem may, for example, be at least generally cylindrical, with a rounded and/or tapered tip to facilitate insertion of the stem into a bore in the ulna. The stem may be configured to be placed in a hole formed in bone obliquely or orthogonally to the medullary canal and/or may be placed along the medullary canal of the ulna, among others.

Outer surface 92 of ulnar prosthesis 54 may have any suitable shape in the region of articulation with the sigmoid fossa or a radial prosthesis. For example, the region of articulation may be substantially spherical or cylindrical, among others. In some embodiments, a region of outer surface 92 that articulates with a radial prosthesis or the natural radius in the distal radioulnar joint may have a dorsal-volar curvature that is greater (i.e., a smaller radius of curvature) than the dorsal-volar curvature of radial prosthesis 52 (e.g., see FIG. 2). Body 164 also may (or may not) form a tail 168 that extends proximally from the majority of the body (see FIG. 1).

Any bone-contacting surface of a prosthesis that abuts subchondral bone may be modified to promote bone ingrowth and/or adhesion to bone. Exemplary bone-contacting surfaces include inner surface 162 and stem 166 of ulnar prosthesis 54, and inner surface 96 and, optionally, side surfaces 98 of radial prosthesis 52. Exemplary modification may include plasma treatment, grit-blasting, or the like. Also, a bone-contacting surface of a prosthesis that abuts subchondral bone may be attached to bone with an adhesive (e.g., bone cement), which may be used alternatively or in addition to one or more fasteners.

II. Method of Surface Replacement of a Distal Radioulnar Joint

The present disclosure provides a method of replacing at least one surface region of a distal radioulnar joint. The method may utilize any suitable combination and order of the steps presented in this Section and elsewhere in the present disclosure. FIGS. 13-22 show exemplary configurations corresponding to and/or illustrating exemplary steps that may be performed in a method of replacing at least one articulation surface region of a distal radioulnar joint with a prosthetic surface region. Installation and attachment of the radial and ulnar prostheses of system 50 (FIG. 1) are shown in these figures.

FIG. 13 shows a dorsal view of the distal region of radius 56 and ulna 58 of a patient's right forearm during establishment of a linear datum or guide axis 180 to facilitate proper resection of bone, and location and attachment of components of system 50. Distal ulna 58 and distal radioulnar joint 51 may be accessed through soft tissue from the dorsal/medial side or the volar/medial side, among others.

To establish datum 180, an elongate guide member 182, such as a stiff wire (e.g., a K-wire of about 1 to 2 mm, such as a 0.062 inch (1.6 mm) K-wire) or a pin, may be inserted into the ulna and radius in a generally medial to lateral direction, from an insertion point originating on the medial side of the head of the distal ulna. A leading end 184 of the guide member may be placed through distal radioulnar joint 51 and particularly through radial and ulnar articulation surfaces thereof, to define datum 180 through the joint and with respect to other surfaces of radius 56 and ulna 58. The guide member may be placed orthogonally to the longitudinal axes of radius 56 and ulna 58 or may be placed obliquely, as shown in FIG. 13, with a proximal to distal slant. Exemplary non-orthogonal angles of placement include about 5-35, 10-30, 15-25, or 20 degrees, among others.

The placement of guide member 182 may be performed free-hand or may be facilitated with an aiming tool 190. The aiming tool may be generally C-shaped, with a body 192 of adjustable and fixable length connected to opposing arms 194, 196, to form a clamp. The position of the arms may be fixed using a locking knob 198, such that the aiming tool can be compressed against and clamped to the forearm. First arm 194 may define a bore 200 that receives and orients the guide member. The bore may define a linear axis that intersects a predefined site, such as a finger 202 on second arm 196. In use, first arm 194 may be placed against a medial surface site of the head of the distal ulna and finger 202 placed against skin (or bone) over a lateral site on the distal radius, and then tool 190 may be clamped in position. A fluoroscope also or alternatively may be utilized during placement of the guide member to monitor positioning and to ensure a desired (e.g., centered) placement through the joint and bone.

FIG. 14 shows a dorsal view of radius 56 and ulna 58 of FIG. 13 with guide member 182 partially withdrawn, indicated at 210, and as an osteotomy is being performed on ulna 58 with a cutting tool 212, such as a saw. In other words, assuming that the ulna is intact, a shaft region 214 of ulna 58 may be cut transversely (orthogonally or obliquely to the long axis of the ulna), completely through the bone, to form distal ulnar fragment 68 and a proximal ulnar fragment 70. The distal ulna may be cut proximal to its distal head 216 by a suitable distance, such as about three inches (76 mm) or so, or no more than about three inches, from a distal tip 218 thereof, which may leave intact ligaments 80, tendons, blood vessels, and the like that connect the radius 56 and ulna 58.

FIG. 15 shows a dorsal view of radius 56 and ulna 58 after osteotomy of the ulna (FIG. 14) and with distal ulnar fragment 68 disposed in a spaced configuration relative to proximal ulnar fragment, such as disposed in a reflected configuration (also termed a pivoted configuration or hinged-out configuration), indicated at 230. Separation of the ulnar fragments may be achieved by moving distal ulnar fragment 68 away from proximal ulnar fragment 70. For example, distal ulnar fragment 68 may be moved by pivoting the ulnar fragment generally medially and away from radius 56 and proximal ulnar fragment 70, to a reflected configuration. The reflected configuration may represent reorientation of distal ulnar fragment 68 by any suitable angle, such as at least about 20, 40, 60, or 90 degrees, among others. Also, another guide member 232 may be placed into a channel 234 in radius 56 formed by guide member 182 (also see FIG. 13).

Generally, in the reflected configuration, the blood supply of the distal ulnar fragment may be maintained by the richly vascularized attachment of the TFC, and the surrounding capsular attachments to the intact periosteal sleeve. In other words, the reflected configuration may not strip the distal ulnar fragment of its blood supply, thereby avoiding avascular necrosis.

FIG. 16 shows a medial view of radius 56 and ulna 58 with the bones positioned as in FIG. 15 and with an etching tool 240, also termed a box chisel, operatively disposed on sigmoid fossa 102. Tool 240 may define an opening 242 that receives guide member 232 (see FIG. 15), to provide proper proximal-distal and dorsal-volar positioning of tool 240 with respect to datum 180 (see FIG. 13). The etching tool may be used to delineate (and cut) a boundary or margin for the surface region of the sigmoid fossa that is to be replaced. Tool 240 can be used as a guide in sizing and shaping a region of the sigmoid fossa to be prepared to receive an available size of radial prosthesis 52. Tool 240 may include a head 244 that defines opening 242 and that is connected to a graspable handle 246. Head 244 may be equipped with a blade 248, which may correspond in shape to the radial prosthesis. With tool 240 properly positioned on sigmoid fossa 102, a surgeon may strike head 244, for example, with a mallet, to drive blade 248 into the sigmoid fossa and thus define a boundary of a surface region 250 of the sigmoid fossa to be excavated. Further aspects of etching tool 240 are described below.

FIG. 17 shows a medial view of radius 56 after use of etching tool 240 to mark or cut a boundary 252 around surface region 250 (also see FIG. 16). An excavation tool 254, such as a power drill fitted with a burr 256, may be used to form a cavity 258 in sigmoid fossa 102. The size and shape of the cavity may be defined by boundary 252. The depth of cavity 258 may correspond to the thickness of the radial prosthesis that will be implanted in the cavity.

FIG. 18 shows a medial view of radius 56 after placement of radial prosthesis 52 in cavity 258 and attachment to the radius with fasteners 60. In other examples, radial prosthesis 52 may be installed after ulnar prosthesis 54 (see FIG. 1) or may be utilized without an ulnar prosthesis in a hemiarthroplasty. In other words, in a repair in which ulna 56 is not otherwise impacted, with radial prosthesis installed, the ulna may be reassembled using a fixation device and fasteners (e.g., a bone plate and bone screws) and the site closed.

Figure 22:
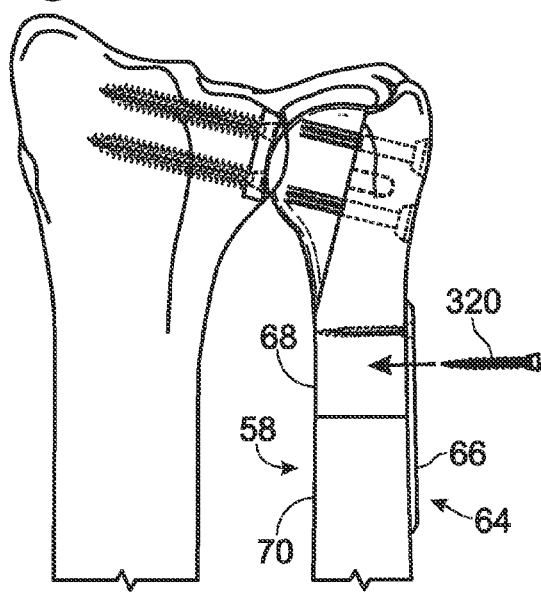

FIGS. 19-22 show dorsal views of radius 56 and ulna 58 as the ulna is drilled (or prepared for drilling) (FIGS. 19 and 21), resected (FIG. 20), and fixed (FIG. 22). These procedures may be performed on the ulna in any suitable order. Also, any of the procedures may be performed on the ulna before or after the radius is excavated and a radial prosthesis implanted. Further, any of the procedures may be performed in a hemiarthroplasty of the distal radioulnar joint.

FIG. 19 illustrates insertion of guide pins 270, 272 into ulna 58 from a medial side thereof, to define paths for drilling into the ulna. A template 274 may be utilized to place guide pins 270, 272. The template may define a bore 276 to receive guide member 182 and one more other bores 278, 280 to position and guide insertion of guide pins 270, 272. Bores 278, 280 of template 274 may be arranged in correspondence with features on ulnar prosthesis 54 (see FIGS. 1 and 2). For example, bores 278, 280 may be spaced to match the separation of threaded apertures 160 of ulnar prosthesis 54 (see FIG. 1).

After placement of guide pins 270, 272 into bone, template 274 may be removed, and holes 282, 284 may be formed by drilling over the guide pins with a cannulated drill bit.

FIG. 20 illustrates resection of a lateral portion of distal head 216 of ulna 58. A cutting guide 290 may be received on guide member 182 to position a guide slot 292 (or a guide face) adjacent a dorsal (or volar) surface of the distal ulna. The guide slot may be disposed at any suitable angle, such as about 10-30 degrees or about 20 degrees, among others, with respect to the longitudinal axis of the ulna. The guide slot (or guide face) may define a cutting plane that extends from a more proximal lateral surface region 294 of the ulna, which may be proximal to head 216, to a distal end surface region 296 of head 216, which may be disposed laterally adjacent ulnar fovea 298 and medially past the central longitudinal axis of the ulna. A cutting tool 300, such as a power saw (e.g., a reciprocating power saw), may remove a resected portion 302 of the ulna guided by slot 292. In some embodiments, a lateral portion of the ulnar head may be removed (resected) before the ulna is cut into proximal and distal segments (e.g., see FIG. 14).

FIG. 21 illustrates drilling a hole 310 in ulna 58 to receive stem 166 of ulnar prosthesis 54 (e.g., see FIG. 1). Hole 310 may be concentric with datum 180 and may be formed by drilling over guide member 182 with a cannulated drill bit 312. Drilling may be performed from the lateral side of ulna 58, with the ulna in a reflected configuration after the ulna has been cut into proximal and distal segments.

FIG. 22 illustrates reassembly of ulna 58 using fixation device 64, namely, bone plate 66 secured with a plurality of bone screws 320. Reassembling ulna 58 may include pivoting distal ulnar fragment 68 from a reflected configuration into axial alignment with proximal ulnar fragment 70. The aligned fragments may be fixed with any suitable fixation device(s), such as a bone plate, one or more bone screws, one or more pins, an external fixator, an intramedullary nail, or any combination thereof, among others.

Figure 23:
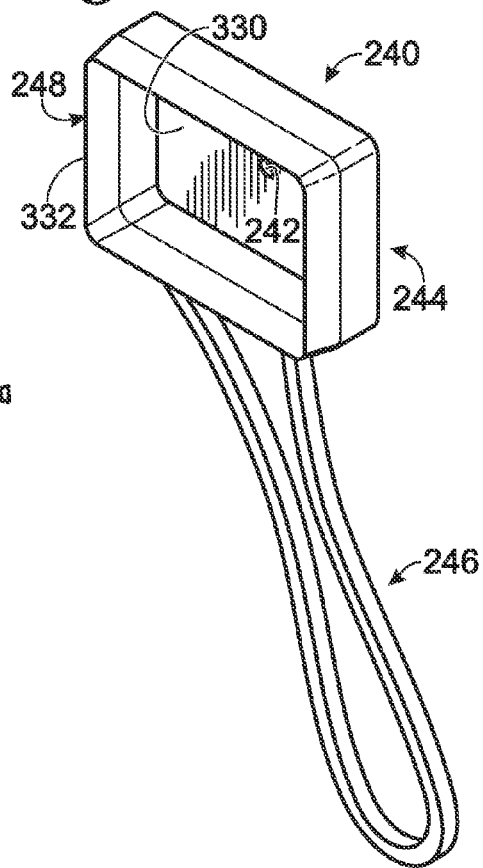
FIG. 23 is an isometric view of the etching tool shown in FIG. 16, taken from the cutting side of the tool.

FIG. 23 shows etching tool 240 from a cutting side of the tool (also see FIG. 16). Tool 240 may include a blade 248 that projects orthogonally from a plate 330 of head 244 to form a cutting edge 332. Blade 248 may extend around the perimeter of the head in a closed loop. The blade may have a depth corresponding to a thickness of the radial prosthesis to be implanted. Advancement of blade 248 into bone may be stopped by contact of plate 330 with bone. Also, blade 248 may circumscribe an area that corresponds in size and shape to a radial prosthesis to be implanted. However, the area may be slightly undersized relative to the size of the radial prosthesis, to obtain a tight fit of the radial prosthesis with bone when implanted.

Figure 24:
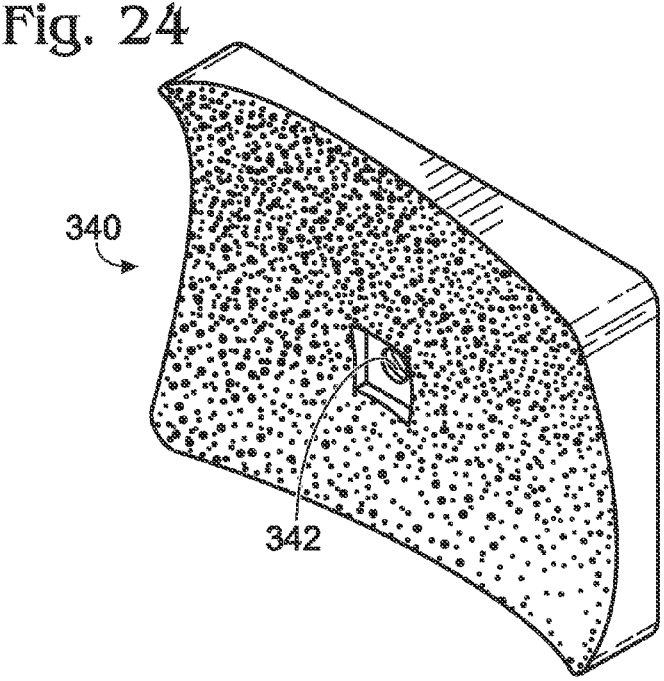
FIG. 24 is an isometric view of an exemplary trial implant that may be implanted provisionally before implantation of a corresponding radial prosthesis in a distal radioulnar joint, in accordance with aspects of the present disclosure.

FIG. 24 shows an exemplary trial implant 340 that may be installed provisionally before installation of a corresponding radial prosthesis in a distal radioulnar joint. Trial implant 340 may correspond generally in size and shape to a radial prosthesis, such as radial prosthesis 52 shown in FIG. 3. Use of a trial implant may permit an appropriate size and/or shape of radial prosthesis to be selected for installation from a set of radial prostheses of distinct size and/or shape. Alternatively, or in addition, use of a trial implant may permit evaluation of the size and shape of a cavity formed in the sigmoid fossa before a radial prosthesis is implanted. Trial implant 340 may define an aperture 342 with an internal thread.

Figure 25:
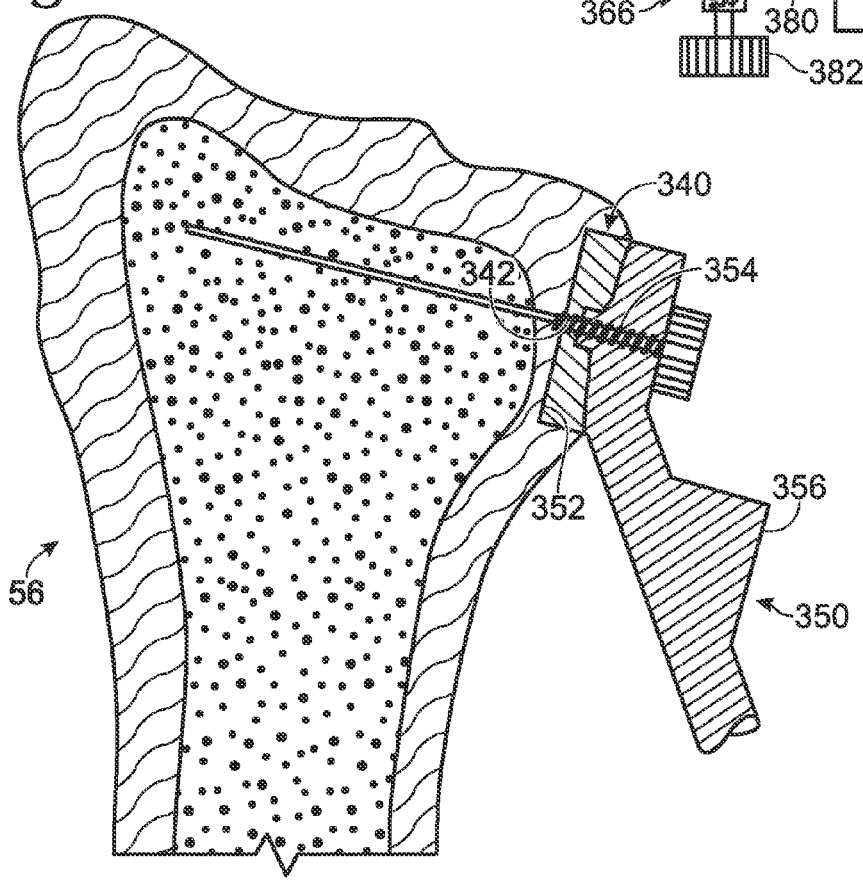
FIG. 25 is a sectional view of the trial implant of FIG. 24 attached to an applicator and installed provisionally in a cavity formed in the sigmoid fossa of a radius, in accordance aspects of the present disclosure.

FIG. 25 shows trial implant 340 attached to a trial applicator 350 and installed provisionally in a cavity 352 formed in the sigmoid fossa of radius 56. Trial implant 340 may be attached to trial applicator 350 by a thumb screw 354 locked to aperture 342. A surface 356 may be provided on applicator 350 for striking with a tool to aid in insertion of the trial implant 340. The applicator may be disconnected from the trial implant to test the fit of the trial implant, and may be re-connected to provide a lever arm for removal of the trial implant.

Figure 26:
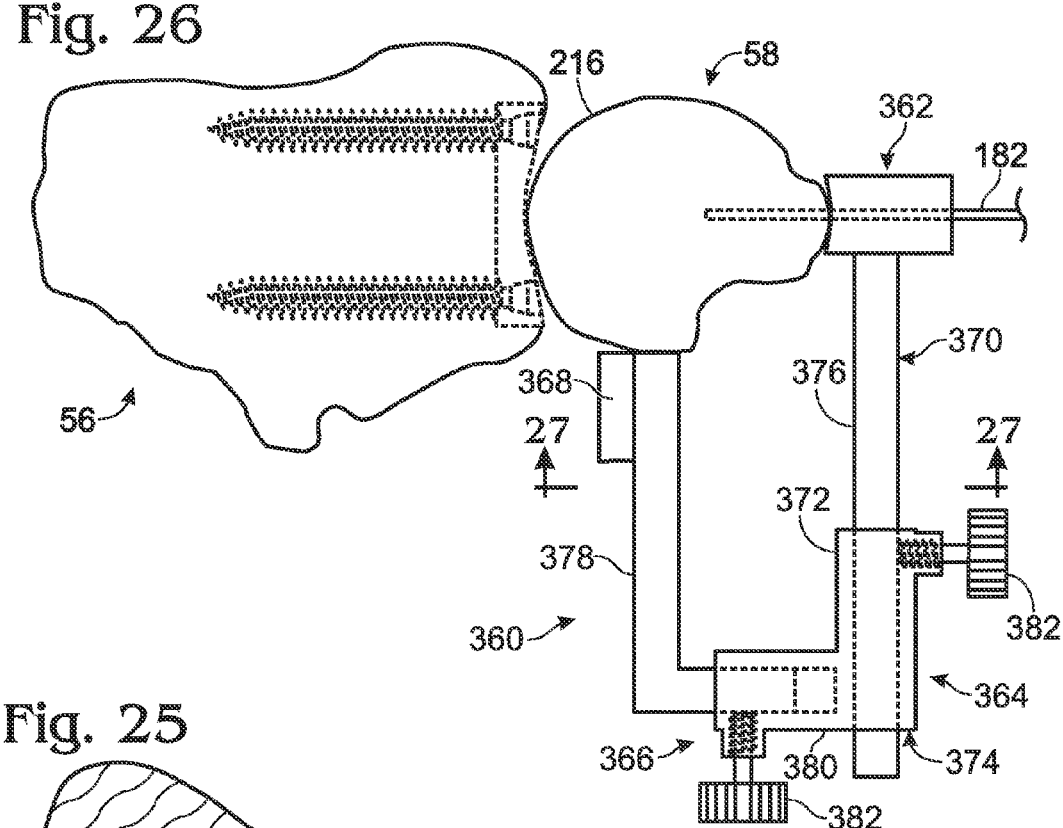
FIG. 26 is a distal view of a radius and an ulna after installation and attachment of the radial prosthesis of FIG. 1 and with an exemplary cutting guide positioned against the ulna and defining a guide path for a saw, in accordance with aspects of the present disclosure.

FIG. 26 shows a distal view of radius 56 and ulna 58 with an exemplary cutting guide 360 positioned against the ulna and defining a guide path for a saw. Cutting guide 360 may be used generally as described for cutting guide 290 of FIG. 20. The cutting guide may include a receiver 362 for guide member 182, a dorsal-volar adjustment mechanism 364, a medial-lateral adjustment mechanism 366, and a guide face 368.

Receiver 362 may include in a T-shaped member 370 that defines a passage to permit member 370 to slide onto guide member 182. A leg 372 of a right-angle elbow 374 may slide onto a free leg 376 of T-shaped member 370 and an L-shaped member 378 carrying guide face 368 may be slid into a remaining leg 380 of elbow 374. A remote end of member 378 carrying guide face 368 may be brought against distal head 216 of the ulna. Thumbscrews 382 on both legs 372, 380 of elbow 374 may be tightened to fix the relative positions of T-shaped member 370 and L-shaped member 378 with respect to elbow 374.

FIG. 27 shows a sectional view of cutting guide 360. Guide face 368 and/or a guide slot 384 may be used to guide a saw blade at an appropriate anatomical angle of, for example, about 20 degrees to the longitudinal axis of ulna 58 to guide partial resection of distal ulnar head 216.

FIGS. 28A and 29A show other exemplary configurations that may be produced during performance of a method of replacing at least one articulation surface region of a distal radioulnar joint.

FIG. 28A shows removal of bone from the sigmoid region of radius 56 to form a cylindrical cavity 390 with a flat bottom. (The radius is illustrated in this view as partially sectional for clarity.) The cavity may be formed by a cannulated bit 392 received on guide member 182 and driven rotationally. Thus, cavity 390 may be centered about guide member 182 (and the linear datum it provides). Bit 392 may be provided, for example, by a drill or an end mill, among others. The depth of cavity 390 may be controlled by a stop 394 formed on bit 392. Alternatively, or in addition, the depth of the cavity may be controlled by eye, such as by observing one or more depth marks 396 formed on a side surface of bit 392, as the cavity is being formed, and comparing the position of the mark(s) relative to an adjacent surface region of bone.

FIG. 28B shows a disc-shaped radial prosthesis 398 that may be implanted in cavity 390. Prosthesis 398 may include a dished outer surface 400 forming a groove 402, as described above for radial prosthesis 52.

FIG. 29A shows use of a box chisel 410 to modify cylindrical cavity 390 to a more polyhedral cavity 412, that is, to make the cavity more square-shaped. Box chisel 410 may have any of the features described above for etching tool 240 (FIG. 16), such as an opening 414 to center a head 416 of the box chisel about guide member 182 (FIG. 13). Head 416 may provide an at least generally square-shaped blade, which may be used to remove corner bone material 418 from adjacent cavity 390. In other words, box chisel 410 may increase the footprint of cavity 390, by expanding the area of its flat bottom without changing the depth of the cavity.

FIG. 29B shows a generally square-shaped radial prosthesis 430 that may be implanted in cavity 412. Prosthesis 430 may include a dished outer surface 432 forming a groove 434, as described above for radial prosthesis 52.

III. Composition of Implants

The implants (prostheses, fixation devices, and/or fasteners) disclosed herein may be formed of any suitable biocompatible material(s). Exemplary biocompatible materials include (1) metals (for example, titanium or titanium alloys, alloys with cobalt and chromium (cobalt-chrome), stainless steel, etc.); (2) plastics/polymers (for example, ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) ceramics (for example, alumina, beryllia, and/or zirconia, among others); (4) composites (e.g., a polymer matrix (such as PEEK) containing carbon fibers and/or ceramic); (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, etc.; and/or the like.

The material(s) constituting a prosthesis for the distal radioulnar joint may be selected based on various considerations. For example, the material may be chosen based on whether the prosthesis is intended to articulate with bone (a hemiarthroplasty) or with another prosthesis (a total arthroplasty) in the joint. Also, or alternatively, the material may be picked based on whether the prosthesis is a one-piece or multi-piece (e.g., two-part) construct.

Exemplary materials for forming a one-piece ulnar prosthesis or one-piece radial prosthesis used in a hemiarthroplasty include titanium, a composite (e.g., PEEK, pyrocarbon, ceramic, etc.), titanium plasma/bead sprayed cobalt-chrome, or the like. Exemplary materials for forming a two-piece ulnar prosthesis or a two-piece radial prosthesis used in a hemiarthroplasty include a back piece formed of titanium and a front piece formed of cobalt-chrome. Thus, metal, composite, or polymer/plastic may articulate with bone in a DRUJ repaired in a hemiarthroplasty.

Exemplary materials used respectively to form a radial prosthesis and an ulnar prosthesis for a total arthroplasty may be the same or different. For example, the radial prosthesis may be formed as a two-piece construct, such as titanium-backed UHMWPE and the ulnar prosthesis as a one-piece construct of titanium plasma/bead sprayed cobalt-chrome, or vice versa. Alternatively, the radial prosthesis may be formed as a one-piece construct of a composite (e.g., PEEK, pyrocarbon, ceramic, etc.) and the ulnar prosthesis as a one-piece construct of a composite (e.g., PEEK, pyrocarbon, ceramic, etc.) or titanium plasma/bead sprayed cobalt-chrome, or vice versa. Moreover, the radial prosthesis and the ulnar prosthesis each may be formed as a one-piece construct of titanium plasma/bead sprayed cobalt-chrome. Furthermore, the radial prosthesis may be formed as a one-piece construct of UHMWPE (e.g., cemented to bone) and the ulnar prosthesis as a one-piece construct of titanium plasma/bead sprayed cobalt-chrome, or vice versa. Thus, a DRUJ repaired by a total arthroplasty may provide articulation of metal on metal, metal on composite, metal on polymer/plastic, composite on composite, composite on polymer/plastic, or polymer/plastic on polymer/plastic, among others.

IV. KITS

Any suitable combination of the system components disclosed herein for surface replacement of the distal radioulnar joint may be provided as a kit. The kit may include at least one radial prosthesis and/or at least one ulnar prosthesis. The prostheses may be configured to articulate with one another in a total arthroplasty and/or with a remaining natural radial or ulnar surface of the distal radioulnar joint in a hemiarthroplasty. One or more of the prostheses may be designed for use in the right distal radioulnar joint or in the left distal radioulnar joint, but not both. Alternatively, or in addition, one or more of the prostheses may be designed for use in both the right and the left distal radioulnar joint.

The kit also may comprise at least fixation device to fix a cut ulna. The fixation device may, for example, be a bone plate configured to span and fix an osteotomy performed on the ulna to facilitate prosthesis installation.

The kit further may incorporate fasteners, such as bone screws, to attach the prostheses and/or the fixation device to bone. Alternatively, or in addition, the kit may be equipped with bone cement for this purpose.

The kit even further may incorporate at least one of, or any combination of, a trial implant, a trial applicator, a cutting guide (to guide a saw or other cutting tool for partial resection of the distal ulnar head (or radial head)), a guide member (e.g., a K-wire or pin), an aiming tool to guide placement of a guide member through the distal radioulnar joint, a template to position guide pins and/or a drill bit(s), a bit(s) to form holes for fasteners and/or to create a cavity for receiving a prosthesis, an etching tool/box chisel, one or more rotary/reciprocating drivers (e.g., to drive placement of the guide member, hole formation, fastener insertion, sawing of bone, etc.), a retraction device to hold a distal ulnar fragment in a reflected configuration, instructions for use, etc.

The kit components may be contained in a case and/or may be packaged individually or in groups. Individual kit components may or may not be provided in a sterile condition. Some of the components (for example, an implanted component) may be designed for single-use, while others (e.g., tools and other installation accessories) may be re-used.

In some examples, the kit may include a set of radial prostheses and/or a set of ulnar prostheses of different sizes and/or shapes. The different sizes and/or shapes of a set may accommodate different anatomies in the population and/or may permit a surgeon to choose a best-fit for a particular surgery. Selection of a best fit may be performed by eye, by measurement, and/or by testing, among others.

A kit may be provided for repairing a distal radioulnar joint formed by a radius and an ulna. The kit may comprise at least one prosthesis selected from a radial prosthesis, an ulnar prosthesis, or both, to replace at least one surface region of the distal radioulnar joint. The kit also may comprise a bone plate to fix proximal and distal ulnar fragments relative to each other. In some embodiments, (a) the at least one prosthesis includes a radial prosthesis including an outer surface forming a groove oriented obliquely to each characteristic axis of the radial prosthesis, (b) the at least one prosthesis includes a radial prosthesis and an ulnar prosthesis including respective concave and convex outer surfaces, (c) the kit further comprises at least two radial prostheses of distinct size and/or shape, or at least two ulnar prostheses of distinct size and/or shape, or at least two of both, (d) the kit further comprises at least one trial implant for use in selecting a prosthesis from among a set of prostheses of distinct size and/or shape, and/or for use in evaluating the size and shape of a cavity in which the prosthesis is to be implanted, (e) the kit further comprises an applicator for use in provisionally installing the trial implant, (f) the kit further comprises a cutting guide configured to be positioned against an ulna and defining a guide path for a saw, or (g) any combination of (a) through (f).

V. EXAMPLES

The following examples describe selected aspects and embodiments of the present disclosure, including exemplary radial and ulnar prostheses for the distal radioulnar joint and exemplary methods of installing the prostheses. Any suitable aspects or elements of the prostheses and/or methods may be combined with one another or with any other aspects or elements presented elsewhere in the present disclosure. These examples are included for illustration and are not intended to limit or define the entire scope of the present disclosure.

Example 1

Ulnar Prostheses with an Integral Plate

This example describes exemplary ulnar prostheses equipped with a plate portion extending from a prosthetic head portion; see FIGS. 30 and 31.

FIG. 30 shows a dorsal view of distal ulna 58 with the seat and pole of the distal ulnar head resected and replaced by another exemplary ulnar prosthesis 450. The ulnar prosthesis may include a head portion 452 connected to a plate portion 454.

Head portion 452 may have any suitable features. The head portion may be shaped in at least general correspondence with, and may include a convex replacement surface 456 for, the resected region of the distal ulnar head. Replacement surface 456 may be at least generally spherical or cylindrical, among others. The head portion may be attached to bone using a stem, fasteners, or the like (e.g., see ulnar prosthesis 54 of FIG. 1). The head portion also may be designed to provide soft tissue fixation. In particular, the head portion may define at least one passage 458 (e.g., a "suture hole"), which may be used to receive a suture 460, which may connect soft tissue (e.g., TFC 80) to head portion 452. The passage may, for example, be generally U-shaped, to form an entry site and an exit site for the suture, and may extend between spaced surface positions of the head portion, such as near the distal end of the prosthesis adjacent TFC 80.

Plate portion 454 may be designed to extend axially along the lateral surface of ulna 58. The plate portion may define one or more apertures 462, which may receive fasteners 464, such as bone screws, that attach prosthesis 450 to the ulna.

FIG. 31 shows a dorsal view of distal ulna 58 with the seat and pole of the distal ulnar head resected and replaced by an exemplary ulnar prosthesis 480 that also fixes the ulna. Prosthesis 480 may includes a head portion 482 connected to a plate portion 484. The plate portion may define a plurality of apertures 486, which may receive fasteners 488, such as bone screws, that attach prosthesis 480 to the ulna. Plate portion 484 may twist partway around the ulna as the plate portion extends along the surface of the bone. For example, the plate portion may extend from a lateral surface region 490 to a dorsal (or volar) surface region 492 of the ulna. By reaching to a distinct side of the bone, the plate portion may be designed to extend farther proximally while avoiding extensive damage to an interosseous membrane 494 disposed between the medial surface of the radius and the lateral surface of the ulna. Accordingly, plate portion 484 may be long enough to span a transverse cut 496 through the ulna, which may be introduced in an osteotomy to facilitate prosthesis installation (e.g., see FIGS. 14 and 15).

Example 2

Arthroplasty of the Distal Radioulnar Joint with Reverse Prostheses

This example describes replacement of radial and ulnar surfaces of the distal radioulnar joint with a "reverse" radial prosthesis 500 and a "reverse" ulnar prosthesis 502 that supply respective convex and concave articulation surfaces 504, 506, the reverse of the joint anatomy; see FIG. 32.

Radial prosthesis 500 may have a generally spherical body 508 and a stem 510 projecting from an inner surface 512 of body 508. Body 508 may define apertures that receive fasteners 514 in a "forward" (medial to lateral) direction or a "retrograde" (lateral to medial) direction. In exemplary embodiments, inner surface 512 may be flat and body 508 may be a frustospherical.

Ulnar prosthesis 502 may be secured on a cut surface of ulna 58 using fasteners 516. For example, the prosthesis may have a flat inner surface 518 that abuts a cut face 520 of ulna 58 formed by partial resection of the lateral aspect of the distal ulnar head. Concave articulation surface 506 of the ulnar prosthesis may be dished and may (or may not) have a curvature that is less than that of the radial prosthesis in both proximal-distal directions and dorsal-volar directions. Also, concave articulation surface 506 may form a groove oriented obliquely to the dorsal-volar axis, to guide and encourage longitudinal motion of the ulna as the distal hand is moved between supination and pronation configurations, as described above for radial prosthesis 52 (e.g., FIGS. 3 and 4).

Ulnar prosthesis optionally may include a stem 522 that extends from inner surface 518 of the implant. Stem 522 may define an axis oriented transversely or, as illustrated here, at least substantially parallel to the longitudinal axis of ulna 58.

Example 3

Replacement of the Ulnar Seat and Pole with an Ulnar Cap

Figure 33:
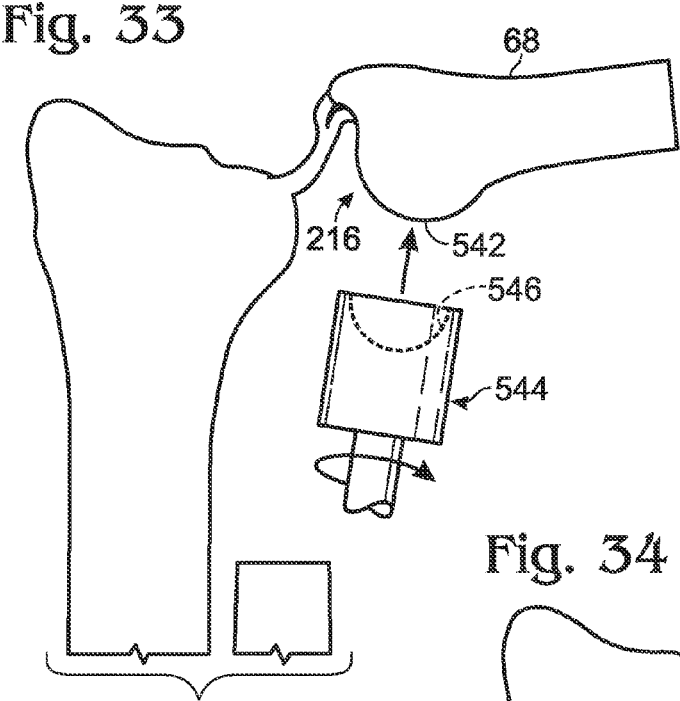
FIGS. 33 and 34 are yet other exemplary configurations that may be produced during performance of a method of replacing at least one surface region of a distal radioulnar joint with a prosthetic surface region.
Figure 34:
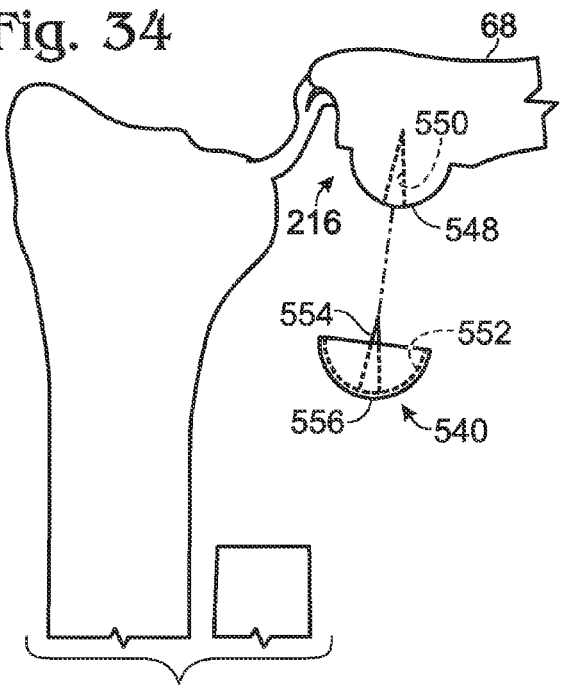

This example describes installation and use of an exemplary ulnar prosthesis 540 structured as an ulnar cap; see FIGS. 33 and 34.

FIG. 33 shows a dorsal view of distal ulnar fragment 68 disposed in a reflected configuration after osteotomy, which exposes an ulnar portion 542 of the distal radioulnar joint to permit resurfacing thereof. A resurfacing bit 544 with a concave reshaping region 546 may be advanced against the lateral aspect of distal ulnar head 216 to modify ulnar portion 542. Rotary action of bit 544 may remove cartilage and/or subchondral bone, to prepare head 216 for receiving ulnar prosthesis 540 (see FIG. 34).

FIG. 34 shows distal ulnar fragment 68 after reshaping head 216 with bit 544 (FIG. 33) to form a lateral knob 548. One or more bores 550 also may be formed in the knob. Ulnar prosthesis 540 then may be installed on knob 548. Prosthesis 540 may have a concave inner surface 552 that is complementary to knob 548 and also may be equipped with a stem 554 that projects from inner surface 552 and that is sized to be impacted or press-fitted into bore 550. Stem 554 may have any suitable shape, such as conical, cylindrical, or the like. Outer surface 556 of prosthesis 540 may be shaped to articulate with a natural or prosthetic radial portion of the distal radioulnar joint.

Example 4

Retrograde and Transverse Attachment of a Radial Prosthesis

Figure 35:
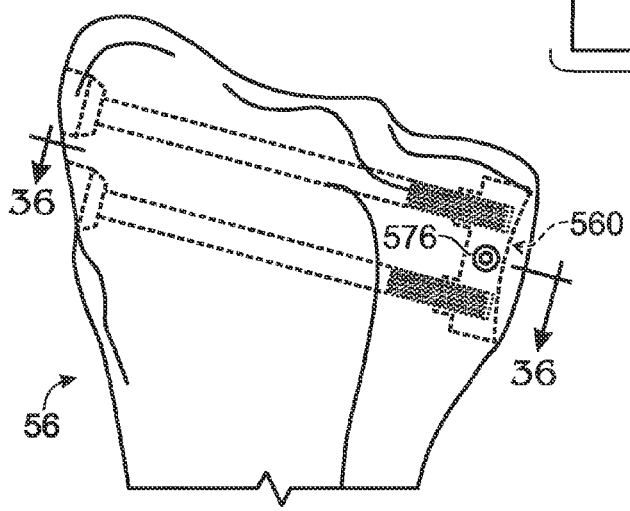
FIG. 35 is a dorsal view of a distal radius bearing yet another exemplary radial prosthesis that replaces the radial portion of a distal radioulnar joint, in accordance with aspects of the present disclosure.

This example describes an exemplary radial prosthesis 560 that can be anchored to the radius with retrograde fasteners and/or a transverse fastener; see FIGS. 35-37.

FIGS. 35 and 36 show respective dorsal and sectional views of radius 56 with radial prosthesis 560 implanted in the sigmoid fossa region of the bone; FIG. 37 shows an isometric view of radial prosthesis 560 alone. Prosthesis 560 may have any of the features described elsewhere herein, such as a dished outer surface 562 for articulation in a distal radioulnar joint.

Prosthesis 560 may be attached to radius 56 with any suitable combination of fasteners. For example, prosthesis 560 may define apertures 564 formed in an inner surface 566. The prosthesis may (or may not) be thicker where the apertures are formed. Each aperture may be locking, to provide threaded engagement with one or more fasteners 568 that extend to the inner surface, such as from a lateral side of radius 56. Prosthesis 560 also may define a transverse aperture 570. Aperture 570 may extend into the prosthesis from a side surface 572, and may be a blind hole or, for example, may extend to an opposing side surface 574 of the prosthesis (FIG. 37). Aperture 570 may or may not be a locking aperture with an internal thread. A transverse fastener 576 may be placed into transverse aperture 570 from a dorsal or a volar side of radius 56 (FIGS. 36 and 37). Fastener 576 may extend through prosthesis 560 for threaded engagement with bone on an opposing side of the prosthesis. Alternatively, or in addition, fastener 576 may lock to transverse aperture 570 with or without extending completely through prosthesis 560.

Example 5

Radial Prosthesis Disposed on Bone

This example describes an exemplary radial prosthesis 590 secured on the distal radius and following natural surface contours of the radius; see FIG. 38.

FIG. 38 shows a distal view of radius 56 bearing radial prosthesis 590. The prosthesis may be structured as a plate that mounts on the radial portion of a distal radioulnar joint to supply a prosthetic radial articulation surface 591 for the distal radioulnar joint. The prosthesis may overlap and extend past the sigmoid fossa region to overlap dorsal and volar surface regions 592, 594 of the radius using respective end regions 596, 598 of the prosthesis. Also, the prosthesis may define one or more apertures 600 in end regions 596, 598 to receive one or more fasteners 602. Each aperture may be locking or nonlocking. Thus, prosthesis 590 may be secured, at least in part, by placing fasteners through apertures 600 from the dorsal and/or volar side of the radius. In some examples, at least a pair of the apertures may be co-axial, to permit placement the leading end region of a fastener through one member of the pair and into threaded engagement with the other member of the pair.

Prosthesis 590 may be placed on and secured to the radius without substantial removal of subchondral bone. In other words, the prosthesis may be installed without formation of a cavity in which the prosthesis is received. Cartilage may (or may not) be removed from the appropriate surface regions of the radius before placement of prosthesis 590 onto bone.

Example 6

Hybrid Bone Plate and Radial Prosthesis

This example describes an exemplary hybrid implant 610 that combines a bone plate for the distal radius with a radial prosthesis; see FIG. 39.

FIG. 39 shows a dorsal view of a fractured distal radius 56 bearing an exemplary implant 610 incorporating a bone plate portion 612 and a radial prosthesis portion 614. The bone plate and radial prosthesis portions may be formed by the same piece (e.g., a monolithic piece) or may be formed by respective, discrete pieces that are attachable to one another. Bone plate portion 612 may be shaped to be received on the dorsal or volar side of a distal radius having one or more fractures 616 (and/or that has been osteotomized), to fix the distal radius. Radial prosthesis portion 614 may furnish a concave, radial articulation surface 618 of a distal radioulnar joint. The radial prosthesis portion may be disposed on the radius or in a cavity formed by removing subchondral bone from the sigmoid fossa region of the radius.

Example 7

Retrograde Attachment of a Radial Prosthesis

This example describes an exemplary radial prosthesis 630 secured in a retrograde direction by a fastener 632 extending through a plate 634 from a lateral side 636 of the distal radius 56; see FIG. 40.

Plate 634 may stabilize fastener 632 by engagement of the head of the fastener. Additional fasteners 638 may secure plate 634 to radius 56. Alternatively, plate 634 may be much shorter and may function as a washer for the head of fastener 632.

Example 8

Radial Prosthesis with Plate Stem

This example describes an exemplary radial prosthesis 650 structured as a plate 652; see FIG. 41.

Plate 652 may include a head 654 connected to a stem 656. Head 654 may be shaped generally as shown in FIG. 38 for ulnar prosthesis 590 and may supply a radial articulation surface 658. Also, head 654 may define at least one aperture 660 to receive a fastener 662 that extends at least generally parallel to articulation surface 658, and/or at least generally dorsal-ventrally. Stem 656 also may define one or more apertures 664 to receive fasteners 666. The stem may extend from a medial position on the radius, proximal to head 654, to a dorsal or ventral position on the radius more distal to head 654.

Example 9

Selected Embodiments

This example describes selected embodiments of the present disclosure, presented as a set of indexed paragraphs.

A. A method of repairing a distal radioulnar joint formed by a radius and an ulna, the method comprising: cutting through a shaft region of the ulna to form a proximal ulnar fragment and a distal ulnar fragment; moving the distal ulnar fragment away from the proximal ulnar fragment to a spaced configuration; removing bone from a sigmoid fossa region of the radius, from a generally laterally facing region of the distal ulnar head, or from both, while the distal ulnar fragment is in the spaced configuration; installing a radial prosthesis, an ulnar prosthesis, or both, in place of bone that has been removed, to replace at least one surface region of the distal radioulnar joint; and fixing the proximal and distal ulnar fragments relative to each other.

The method of paragraph (A) also may comprise the following: (i) wherein the step of moving includes a step of pivoting the ulnar fragment away from the proximal ulnar fragment to a reflected configuration, and wherein the step of removing bone is performed while the distal ulnar fragment is in the reflected configuration; (ii) further comprising a step of resecting a lateral portion of the distal ulnar head before the step of removing bone, to form the generally laterally facing region of the distal ulnar head; (iii) wherein the step of resecting is performed before the step of cutting; (iv) wherein the step of resecting forms a cut surface on the distal ulnar head, and wherein the step of removing bone includes a step of removing bone from below the cut surface; (v) wherein the step of removing bone includes a step of forming a cavity in the sigmoid fossa region of the radius, and wherein the step of installing includes a step of placing a radial prosthesis at least partially in the cavity; (vi) wherein the step of installing includes a step of attaching both a radial prosthesis and an ulnar prosthesis to the radius and the ulna, respectively; (vii) wherein attachment of the triangular fibrocartilage complex to the radius and the ulna is not disturbed by any of the steps of cutting, moving, removing, installing, or fixing; (viii) further comprising a step of placing an elongate guide member into the radius and ulna such that the guide member defines a linear datum extending through the joint, wherein the step of removing bone includes a step of positioning a bone-removal tool based on the linear datum, and wherein the step of removing bone optionally includes a step of creating a bone surface oriented orthogonally to the linear datum; (ix) wherein the step of pivoting includes a step of pivoting the distal ulnar fragment at least about 90 degrees with respect to the proximal ulnar fragment; (x) wherein the ulnar prosthesis has a head connected to a stem, and wherein the step of installing disposes the stem in a bore formed in the ulna, and, optionally, further comprising a step of forming the bore in the ulna with the bore oriented transversely or orthogonally to a longitudinal axis defined by the ulna; (xi) further comprising a step of provisionally installing a trial implant before the step of installing a radial prosthesis, an ulnar prosthesis, or both; (xii) wherein the step of fixing the proximal and distal ulnar fragments includes a step of securing a bone plate to the two fragments; or (xiii) any combination of (i) through (xii).

B. A method of repairing a distal radioulnar joint formed by a radius and an ulna, the method comprising: cutting through a shaft region of the ulna to form a proximal ulnar fragment and a distal ulnar fragment; pivoting the distal ulnar fragment away from the proximal ulnar fragment to a reflected configuration; forming a cavity in a sigmoid fossa region of the radius while the distal ulnar fragment is in the reflected configuration; attaching a radial prosthesis to the radius with the radial prosthesis at least partially in the cavity, to replace a radial surface region of the distal radioulnar joint; and securing a bone plate to the ulna to fix the proximal and distal ulnar fragments relative to each other. In some embodiments, the radial prosthesis includes an outer surface forming a groove, and the step of attaching disposes the groove such that the groove extends, with respect to the radius, from a more distal position dorsally to a more proximal position volarly.

C. A method of repairing at least a radial side of a distal radioulnar joint formed by a radius and an ulna, the method comprising: selecting a radial prosthesis including an outer surface forming a groove; and attaching the radial prosthesis to the radius such that the outer surface replaces a radial surface region of the distal radioulnar joint, with the groove extending, with respect to the radius, from a more distal position dorsally to a more proximal position volarly. In some embodiments, the step of selecting includes a step of selecting a radial prosthesis including an outer surface that has a perimeter shaped at least generally as a quadrilateral.

D. A method of repairing a distal radioulnar joint formed by a radius and an ulna, the method comprising: placing an elongate guide member into the radius and ulna such that the guide member defines a linear datum extending through the distal radioulnar joint; removing bone, using the linear datum as a reference, from a sigmoid fossa region of the radius and from a generally laterally facing region of the distal ulnar head; and installing a radial prosthesis and an ulnar prosthesis in place of bone that has been removed to replace respective radial and ulnar surface regions of the distal radioulnar joint.

E. A device for repairing a distal radioulnar joint formed by a radius and an ulna, comprising: a radial prosthesis including a dished outer surface forming a groove.

In some embodiments, the device of paragraph (E) also may comprise the following: (i) wherein the outer surface has a compound curvature with a first curvature and a second curvature, and wherein the second curvature is oriented obliquely to the first curvature to form the groove; (ii) wherein the radial prosthesis defines a long axis, and wherein the groove extends obliquely to the long axis; (iii) wherein the radial prosthesis includes an inner surface opposing the outer surface and also includes a side wall connecting the inner and outer surfaces, wherein the side wall defines a longitudinal axis of the side wall, and wherein the groove extends obliquely to the longitudinal axis of the side wall; (iv) wherein the groove extends at an angle of about 10 to 20 degrees with respect to the longitudinal axis of the side wall; (v) further comprising an ulnar prosthesis including a flat surface that faces bone and a stem that projects orthogonally from the flat surface; or (vi) any combination of (i) through (v).

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of repairing a distal radioulnar joint formed by a radius and an ulna, the method comprising:
   cutting through a shaft region of the ulna to form a proximal ulnar fragment and a distal ulnar fragment;
   pivoting the distal ulnar fragment away from the proximal ulnar fragment to a pivoted configuration;
   removing bone from a sigmoid fossa region of the radius, from a generally laterally facing region of the distal ulnar head, or from both, while the distal ulnar fragment is in the pivoted configuration;
   installing a radial prosthesis, an ulnar prosthesis, or both, in place of bone that has been removed, to replace at least one surface region of the distal radioulnar joint; and
   fixing the proximal and distal ulnar fragments relative to each other.

2. The method of claim 1, further comprising a step of resecting a lateral portion of the distal ulnar head before the step of removing bone, to form the generally laterally facing region of the distal ulnar head.

3. The method of claim 2, wherein the step of resecting is performed before the step of cutting.

4. The method of claim 2, wherein the step of resecting forms a cut surface on the distal ulnar head, and wherein the step of removing bone includes a step of removing bone from below the cut surface.

5. The method of claim 1, wherein the step of removing bone includes a step of forming a cavity in the sigmoid fossa region of the radius, and wherein the step of installing includes a step of placing a radial prosthesis at least partially in the cavity.

6. The method of claim 1, wherein the step of installing includes a step of attaching both a radial prosthesis and an ulnar prosthesis to the radius and the ulna, respectively.

7. The method of claim 1, wherein attachment of the triangular fibrocartilage complex to the radius and the ulna is not disturbed by any of the steps of cutting, pivoting, removing, installing, or fixing.

8. The method of claim 1, further comprising a step of placing an elongate guide member into the radius and ulna such that the guide member defines a linear datum extending through the joint, wherein the step of removing bone includes a step of positioning a bone-removal tool based on the linear datum.

9. The method of claim 8, wherein the step of removing bone includes a step of creating a bone surface oriented orthogonally to the linear datum.

10. The method of claim 1, wherein the step of pivoting includes a step of pivoting the distal ulnar fragment at least about 90 degrees with respect to the proximal ulnar fragment.

11. The method of claim 1, wherein the ulnar prosthesis has a head connected to a stem, and wherein the step of installing disposes the stem in a bore formed in the ulna.

12. The method of claim 11, further comprising a step of forming the bore in the ulna with the bore oriented transversely or orthogonally to a longitudinal axis defined by the ulna.

13. The method of claim 1, further comprising a step of provisionally installing a trial implant before the step of installing a radial prosthesis, an ulnar prosthesis, or both.

14. The method of claim 1, wherein the step of fixing the proximal and distal ulnar fragments includes a step of securing a bone plate to the two fragments.

15. A method of repairing a distal radioulnar joint formed by a radius and an ulna, the method comprising:
    cutting through a shaft region of the ulna to form a proximal ulnar fragment and a distal ulnar fragment;
    pivoting the distal ulnar fragment away from the proximal ulnar fragment to a pivoted configuration;
    forming a cavity in a sigmoid fossa region of the radius while the distal ulnar fragment is in the pivoted configuration;
    attaching a radial prosthesis to the radius with the radial prosthesis at least partially in the cavity, to replace a radial surface region of the distal radioulnar joint; and
    securing a bone plate to the ulna to fix the proximal and distal ulnar fragments relative to each other.

16. The method of claim 15, wherein the radial prosthesis includes an outer surface forming a groove, and wherein the step of attaching disposes the groove such that the groove extends, with respect to the radius, from a more distal position dorsally to a more proximal position volarly.

17. A method of repairing a distal radioulnar joint formed by a radius and an ulna, the method comprising:
    cutting through a shaft region of the ulna to form a proximal ulnar fragment and a distal ulnar fragment;
    moving the distal ulnar fragment away from the proximal ulnar fragment to a spaced configuration;
    removing bone from a sigmoid fossa region of the radius, from a generally laterally facing region of the distal ulnar head, or from both, while the distal ulnar fragment is in the spaced configuration;
    installing a radial prosthesis, an ulnar prosthesis, or both, in place of bone that has been removed, to replace at least one surface region of the distal radioulnar joint;
    fixing the proximal and distal ulnar fragments relative to each other; and
    resecting a lateral portion of the distal ulnar head before the step of removing bone, to form the generally laterally facing region of the distal ulnar head.

18. The method of claim 17, wherein the step of removing bone includes a step of forming a cavity in the sigmoid fossa region of the radius, and wherein the step of installing includes a step of placing a radial prosthesis at least partially in the cavity.

19. The method of claim 17, wherein the step of installing includes a step of attaching both a radial prosthesis and an ulnar prosthesis to the radius and the ulna, respectively.

20. The method of claim 17, wherein the step of fixing the proximal and distal ulnar fragments includes a step of securing a bone plate to the two fragments.

21. The method of claim 17, wherein the ulnar prosthesis has a head connected to a stem, and wherein the step of installing disposes the stem in a bore formed in the ulna.

22. The method of claim 21, further comprising a step of forming the bore in the ulna with the bore oriented transversely or orthogonally to a longitudinal axis defined by the ulna.

23. The method of claim 17, wherein the radial prosthesis includes an outer surface forming a groove, and wherein the step of installing attaches the radial prosthesis to the radius and disposes the groove such that the groove extends, with respect to the radius, from a more distal position dorsally to a more proximal position volarly.

24. A method of repairing a distal radioulnar joint formed by a radius and an ulna, the method comprising:
    cutting through a shaft region of the ulna to form a proximal ulnar fragment and a distal ulnar fragment;
    moving the distal ulnar fragment away from the proximal ulnar fragment to a spaced configuration;
    removing bone from a sigmoid fossa region of the radius, from a generally laterally facing region of the distal ulnar head, or from both, while the distal ulnar fragment is in the spaced configuration;
    installing a radial prosthesis, an ulnar prosthesis, or both, in place of bone that has been removed, to replace at least one surface region of the distal radioulnar joint; and
    fixing the proximal and distal ulnar fragments relative to each other,
    wherein attachment of the triangular fibrocartilage complex to the radius and the ulna is not disturbed by any of the steps of cutting, moving, removing, installing, or fixing.

25. The method of claim 24, wherein the ulnar prosthesis has a head connected to a stem, and wherein the step of installing disposes the stem in a bore formed in the ulna, further comprising a step of forming the bore in the ulna with the bore oriented transversely or orthogonally to a longitudinal axis defined by the ulna.

26. The method of claim 24, wherein the radial prosthesis includes an outer surface forming a groove, and wherein the step of installing attaches the radial prosthesis to the radius and disposes the groove such that the groove extends, with respect to the radius, from a more distal position dorsally to a more proximal position volarly.

27. A method of repairing a distal radioulnar joint formed by a radius and an ulna, the method comprising:
cutting through a shaft region of the ulna to form a proximal ulnar fragment and a distal ulnar fragment;
moving the distal ulnar fragment away from the proximal ulnar fragment to a spaced configuration;
removing bone from a sigmoid fossa region of the radius, from a generally laterally facing region of the distal ulnar head, or from both, while the distal ulnar fragment is in the spaced configuration;
installing a radial prosthesis, an ulnar prosthesis, or both, in place of bone that has been removed, to replace at least one surface region of the distal radioulnar joint;
fixing the proximal and distal ulnar fragments relative to each other; and
placing an elongate guide member into the radius and ulna such that the guide member defines a linear datum extending through the joint,
wherein the step of removing bone includes a step of positioning a bone-removal tool based on the linear datum.

28. The method of claim 27, wherein the ulnar prosthesis has a head connected to a stem, and wherein the step of installing disposes the stem in a bore formed in the ulna, further comprising a step of forming the bore in the ulna with the bore oriented transversely or orthogonally to a longitudinal axis defined by the ulna.

29. The method of claim 27, wherein the radial prosthesis includes an outer surface forming a groove, and wherein the step of installing attaches the radial prosthesis to the radius and disposes the groove such that the groove extends, with respect to the radius, from a more distal position dorsally to a more proximal position volarly.

30. A method of repairing a distal radioulnar joint formed by a radius and an ulna, the method comprising:
cutting through a shaft region of the ulna to form a proximal ulnar fragment and a distal ulnar fragment;
moving the distal ulnar fragment away from the proximal ulnar fragment to a spaced configuration;
removing bone from a sigmoid fossa region of the radius, from a generally laterally facing region of the distal ulnar head, or from both, while the distal ulnar fragment is in the spaced configuration;
installing a radial prosthesis, an ulnar prosthesis, or both, in place of bone that has been removed, to replace at least one surface region of the distal radioulnar joint; and
fixing the proximal and distal ulnar fragments relative to each other,
wherein the ulnar prosthesis has a head connected to a stem, and wherein the step of installing disposes the stem in a bore formed in the ulna, further comprising a step of forming the bore in the ulna with the bore oriented transversely or orthogonally to a longitudinal axis defined by the ulna.

31. The method of claim 30, wherein the radial prosthesis includes an outer surface forming a groove, and wherein the step of installing attaches the radial prosthesis to the radius and disposes the groove such that the groove extends, with respect to the radius, from a more distal position dorsally to a more proximal position volarly.

* * * * *